US009079972B2

(12) United States Patent
Matsubara et al.

(10) Patent No.: US 9,079,972 B2
(45) Date of Patent: Jul. 14, 2015

(54) METHOD OF SCREENING A SUBSTANCE FOR IMPROVING INSULIN RESISTANCE

(75) Inventors: Toshiya Matsubara, Nishinomiya (JP); Osamu Nishimura, Kawanishi (JP); Susumu Iwasa, Kyotanabe (JP); Makoto Watanabe, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 13/370,840

(22) Filed: Feb. 10, 2012

(65) Prior Publication Data

US 2012/0149026 A1 Jun. 14, 2012

Related U.S. Application Data

(62) Division of application No. 12/610,977, filed on Nov. 2, 2009, now abandoned.

(51) Int. Cl.

| | |
|---|---|
| ***G01N 33/53*** | (2006.01) |
| ***C07K 14/52*** | (2006.01) |
| ***C07K 14/475*** | (2006.01) |
| ***C12Q 1/68*** | (2006.01) |
| ***G01N 33/68*** | (2006.01) |

(52) U.S. Cl.

CPC ............... *C07K 14/52* (2013.01); *C07K 14/475* (2013.01); *C12Q 1/6883* (2013.01); *G01N 33/68* (2013.01); *C12Q 2600/136* (2013.01); *C12Q 2600/158* (2013.01); *G01N 2500/04* (2013.01); *G01N 2500/10* (2013.01); *G01N 2800/042* (2013.01)

(58) Field of Classification Search

None

See application file for complete search history.

(56) References Cited

U.S. PATENT DOCUMENTS

| | | | | |
|---|---|---|---|---|
| 8,563,261 | B2 * | 10/2013 | Chacko ........................ | 435/7.92 |
| 2004/0241802 | A1 | 12/2004 | Kadowaki et al. | |
| 2006/0110384 | A1 | 5/2006 | Matsuzawa et al. | |
| 2006/0199761 | A1 | 9/2006 | Kadowaki et al. | |

FOREIGN PATENT DOCUMENTS

| | | | |
|---|---|---|---|
| JP | 2004-105175 | A | 4/2004 |
| JP | 2004-135605 | A | 5/2004 |
| JP | 2005-247740 | A | 9/2005 |
| JP | 2006-141233 | A | 6/2006 |
| JP | 2009-204475 | A | 9/2009 |
| WO | WO-03/063894 | A1 | 8/2003 |
| WO | WO-2004/061108 | A1 | 7/2004 |

OTHER PUBLICATIONS

Green, Howard et al., "An Established Preadipose Cell Line and Its Differentiation in Culture II. Factors Affecting the Adipose Conversion", Cell, 1975, vol. 5, pp. 19-27.

Fasshauer, Mathias et al., "Hormonal Regulation of Adiponectin Gene Expression in 3T3-L1 Adipocytes", Biochemical and Biophysical Research Communications, 2002, vol. 290, No. 3, pp. 1084-1089.

Yamauchi, T. et al., "The Fat-Derived Hormone Adiponectin Reverses Insulin Resistance Associated with Both Lipoatrophy and Obesity", Nature Medicine, 2001, vol. 7, No. 8, pp. 941-946.

Flier, Jeffrey S., "Diabetes: The Missing Link with Obesity?" Nature, 2001, vol. 409, pp. 292-293.

Fasshauer, Mathias et al., "Tumor Necrosis Factor α Is a Negative Regulator of Resistin Gene Expression and Secretion in 3T3-L1 Adipocytes", Biochemical and Biophysical Research Communications, 2001, vol. 288, No. 4, pp. 1027-1031.

Nguyen, M.T. Audrey et al., "JNK and Tumor Necrosis Factor-α Mediate Free Fatty Acid-Induced Insulin Resistance in 3T3-L1 Adipocytes", The Journal of Biological Chemistry, 2005, vol. 280, No. 42, pp. 35361-35371.

Tanaka, Masaki et al., "Visfatin is Released from 3T3-L1 Adipocytes Via a Non-Classical Pathway", Biochemical and Biophysical Research Communications, 2007, vol. 359, pp. 194-201.

Hotamisligil, Gökhan S. et al., "Tumor Necrosis Factor α Inhibits Signaling from the Insulin Receptor", The Proceedings of the National Academy of Sciences, 1994, vol. 91, pp. 4854-4858.

Sakoda, Hideyuki et al., "Dexamethasone-Induced Insulin Resistance in 3T3-L1 Adipocytes Is Due to Inhibition of Glucose Transport Rather Than Insulin Signal Tranduction", Diabetes, 2000, vol. 49, pp. 1700-1708.

Avruch, Joseph, "Insulin Signal Transduction Through Protein Kinase Cascades", Molecular and Cellular Biochemistry, 1998, vol. 182, pp. 31-48.

Combettes-Souverain, M. et al., "Molecular Basis of Insulin Action", Diabetes & Metabolism (Paris), 1998, vol. 24, No. 6, pp. 477-489.

Kahn, Barbara B., "Type 2 Diabetes: When Insulin Secretion Fails to Compensate for Insulin Resistance", Cell, 1998, vol. 92, pp. 593-596.

Virkamäki, Antti et al., "Protein-Protein Interaction in Insulin Signaling and the Molecular Mechanisms of Insulin Resistance", The Journal of Clinical Investigation, 1999, vol. 103, No. 7, pp. 931-943.

He, Zhiheng et al., "Progranulin (Granulin-Epithelin Precursor, PC-Cell-Derived Growth Factor, Acrogranin) Mediates Tissues Repair and Tumorigenesis", Journal of Molecular Medicine, 2003, vol. 81, pp. 600-612.

Zhou, Jian et al., "Purification of an Autocrine Growth Factor Homologous with Mouse Epithelin Precursor from a Highly Tumorigenic Cell Line", The Journal of Biological Chemistry, 1993, vol. 268, No. 15, pp. 10863-10869.

* cited by examiner

*Primary Examiner* — Christine J Saoud

(74) *Attorney, Agent, or Firm* — Cheng Law Group, PLLC

(57) ABSTRACT

An insulin resistance marker, a method of evaluating insulin resistance, a method of screening a substance that improves insulin resistance, and a pharmaceutical composition for improving insulin resistance are provided. The insulin resistance marker includes a polypeptide comprising at least any 15 continuous amino acids in the specific amino acid sequence of SEQ ID NO: 1 (sequence of a proepithelin protein). The insulin resistance marker includes a polynucleotide selected from the group consisting of (1) a polynucleotide comprising at least any 45 continuous bases in the base sequence of SEQ ID NO:2 encoding the above specific amino acid sequence, and (2) a polynucleotide that is complementary to the polynucleotide of (1).

1 Claim, 8 Drawing Sheets mean ± S.D., n=4, p-value : ** < 0.05 mean ± S.D., n=4, p-value : ** < 0.05

SEQUENCE LISTING

<160> NUMBER OF SEQ ID NOS: 4

<210> SEQ ID NO 1
<211> LENGTH: 593
<212> TYPE: PRT
<213> ORGANISM: human

<400> SEQUENCE: 1

```
Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365
```

```
Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu


<210> SEQ ID NO 2
<211> LENGTH: 1782
<212> TYPE: DNA
<213> ORGANISM: human

<400> SEQUENCE: 2

atgtggaccc tggtgagctg ggtggcctta acagcagggc tggtggctgg aacgcggtgc      60

ccagatggtc agttctgccc tgtggcctgc tgcctggacc ccggaggagc cagctacagc     120

tgctgccgtc cccttctgga caaatggccc acaacactga gcaggcatct gggtggcccc     180

tgccaggttg atgcccactg ctctgccggc cactcctgca tctttaccgt ctcagggact     240

tccagttgct gccccttccc agaggccgtg gcatgcgggg atggccatca ctgctgccca     300

cggggcttcc actgcagtgc agacgggcga tcctgcttcc aaagatcagg taacaactcc     360

gtgggtgcca tccagtgccc tgatagtcag ttcgaatgcc cggacttctc cacgtgctgt     420

gttatggtcg atggctcctg ggggtgctgc cccatgcccc aggcttcctg ctgtgaagac     480

agggtgcact gctgtccgca cggtgccttc tgcgacctgg ttcacacccg ctgcatcaca     540

cccacgggca cccacccccct ggcaaagaag ctccctgccc agaggactaa cagggcagtg     600

gccttgtcca gctcggtcat gtgtccggac gcacggtccc ggtgccctga tggttctacc     660

tgctgtgagc tgcccagtgg gaagtatggc tgctgcccaa tgcccaacgc cacctgctgc     720

tccgatcacc tgcactgctg cccccaagac actgtgtgtg acctgatcca gagtaagtgc     780

ctctccaagg agaacgctac cacggacctc ctcactaagc tgcctgcgca cacagtgggg     840
```

```
gatgtgaaat gtgacatgga ggtgagctgc ccagatggct atacctgctg ccgtctacag    900

tcgggggcct ggggctgctg cccttttacc caggctgtgt gctgtgagga ccacatacac    960

tgctgtcccg cggggtttac gtgtgacacg cagaagggta cctgtgaaca ggggccccac   1020

caggtgccct ggatggagaa ggccccagct cacctcagcc tgccagaccc acaagccttg   1080

aagagagatg tcccctgtga taatgtcagc agctgtccct cctccgatac ctgctgccaa   1140

ctcacgtctg ggagtgggg ctgctgtcca atcccagagg ctgtctgctg ctcggaccac   1200

cagcactgct gcccccaggg ctacacgtgt gtagctgagg ggcagtgtca gcgaggaagc   1260

gagatcgtgg ctggactgga gaagatgcct gcccgccggg cttccttatc ccaccccaga   1320

gacatcggct gtgaccagca caccagctgc ccggtggggc agacctgctg cccgagcctg   1380

ggtgggagct gggcctgctg ccagttgccc catgctgtgt gctgcgagga tcgccagcac   1440

tgctgcccgg ctggctacac ctgcaacgtg aaggctcgat cctgcgagaa ggaagtggtc   1500

tctgcccagc ctgccacctt cctggcccgt agccctcacg tgggtgtgaa ggacgtggag   1560

tgtggggaag gacacttctg ccatgataac cagacctgct gccgagacaa ccgacagggc   1620

tgggcctgct gtccctaccg ccagggcgtc tgttgtgctg atcggcgcca ctgctgtcct   1680

gctggcttcc gctgcgcagc caggggtacc aagtgtttgc gcagggaggc cccgcgctgg   1740

gacgcccctt tgagggaccc agccttgaga cagctgctgt ga                      1782
```

<210> SEQ ID NO 3
<211> LENGTH: 589
<212> TYPE: PRT
<213> ORGANISM: Mus musculus

<400> SEQUENCE: 3

```
Met Trp Val Leu Met Ser Trp Leu Ala Phe Ala Ala Gly Leu Val Ala
1               5                   10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Arg Ile Thr Ser His His Leu Asp Gly Ser Cys Gln Thr His
    50                  55                  60

Gly His Cys Pro Ala Gly Tyr Ser Cys Leu Leu Thr Val Ser Gly Thr
65                  70                  75                  80

Ser Ser Cys Cys Pro Phe Ser Lys Gly Val Ser Cys Gly Asp Gly Tyr
                85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
        115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Arg Ala Val Ser Leu Pro Phe Ser Val Val Cys Pro
        195                 200                 205
```

```
Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300

Cys Pro Phe Ala Lys Ala Val Cys Cys Glu Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Pro Trp Met Lys Lys Val Ile Ala Pro Leu Arg Leu
            340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
            420                 425                 430

Thr Pro Leu Gln Ile Gly Asp Ile Gly Cys Asp Gln His Thr Ser Cys
        435                 440                 445

Pro Val Gly Gln Thr Cys Cys Pro Ser Leu Lys Gly Ser Trp Ala Cys
    450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
            500                 505                 510

Gly Asn Val Glu Cys Gly Glu Gly His Phe Cys His Asp Asn Gln Thr
        515                 520                 525

Cys Cys Lys Asp Ser Ala Gly Val Trp Ala Cys Cys Pro Tyr Leu Lys
    530                 535                 540

Gly Val Cys Cys Arg Asp Gly Arg His Cys Cys Pro Gly Gly Phe His
545                 550                 555                 560

Cys Ser Ala Arg Gly Thr Lys Cys Leu Arg Lys Lys Ile Pro Arg Trp
                565                 570                 575

Asp Met Phe Leu Arg Asp Pro Val Pro Arg Pro Leu Leu
            580                 585
```

<210> SEQ ID NO 4
<211> LENGTH: 1770
<212> TYPE: DNA
<213> ORGANISM: Mus musculus

```
<400> SEQUENCE: 4

atgtgggtcc tgatgagctg gctggccttc gcggcagggc tggtagccgg aacacagtgt      60

ccagatgggc agttctgccc tgttgcctgc tgccttgacc agggaggagc caactacagc     120

tgctgtaacc ctcttctgga cacatggcct agaataacga gccatcatct agatggctcc     180

tgccagaccc atggccactg tcctgctggc tattcttgtc ttctcactgt gtctgggact     240

tccagctgct gcccgttctc taagggtgtg tcttgtggtg atggctacca ctgctgcccc     300

cagggcttcc actgtagtgc agatgggaaa tcctgcttcc agatgtcaga taacccettg     360

ggtgctgtcc agtgtcctgg gagccagttt gaatgtcctg actctgccac ctgctgcatt     420

atggttgatg gttcgtgggg atgttgtccc atgccccagg cctcttgctg tgaagacaga     480

gtgcattgct gtccccatgg ggcctcctgt gacctggttc acacacgatg cgtttcaccc     540

acgggcaccc acaccctact aaagaagttc cctgcacaaa agaccaacag ggcagtgtct     600

ttgccttttt ctgtcgtgtg ccctgatgct aagacccagt gtcccgatga ttctacctgc     660

tgtgagctac ccactgggaa gtatggctgc tgtccaatgc ccaatgccat ctgctgttcc     720

gaccacctgc actgctgccc ccaggacact gtatgtgacc tgatccagag taagtgccta     780

tccaagaact acaccacgga tctcctgacc aagctgcctg gatacccagt gaaggaggtg     840

aagtgcgaca tggaggtgag ctgccctgaa ggatatacct gctgccgcct caacactggg     900

gcctggggct gctgtccatt tgccaaggcc gtgtgttgtg aggatcacat tcattgctgc     960

ccggcagggt ttcagtgtca cacagagaaa ggaacctgcg aaatgggtat cctccaagta    1020

ccctggatga agaaggtcat agcccccctc cgcctgccag acccacagat cttgaagagt    1080

gatacacctt gtgatgactt cactaggtgt cctacaaaca atacctgctg caaactcaat    1140

tctggggact ggggctgctg tcccatccca gaggctgtct gctgctcaga caaccagcat    1200

tgctgccctc agggcttcac atgtctggct caggggtact gtcagaaggg agacacaatg    1260

gtggctggcc tggagaagat acctgcccgc cagacaaccc cgctccaaat tggagatatc    1320

ggttgtgacc agcataccag ctgcccagta gggcaaacct gctgcccaag cctcaaggga    1380

agttgggcct gctgccagct gccccatgct gtgtgctgtg aggaccggca gcactgttgc    1440

ccggccgggt acacctgcaa tgtgaaggcg aggacctgtg agaaggatgt cgattttatc    1500

cagcctcccg tgctcctgac cctcggccct aaggttggga atgtggagtg tggagaaggg    1560

catttctgcc atgataacca gacctgttgt aaagacagtg caggagtctg ggcctgctgt    1620

ccctacctaa agggtgtctg ctgtagagat ggacgtcact gttgccccgg tggcttccac    1680

tgttcagcca ggggaaccaa gtgtttgcga aagaagattc ctcgctggga catgtttttg    1740

agggatccgg tcccaagacc gctactgtaa                                     1770
```

METHOD OF SCREENING A SUBSTANCE FOR IMPROVING INSULIN RESISTANCE

CROSS REFERENCE TO RELATED APPLICATION

This application is a Divisional Application of patent application Ser. No. 12/610,977, filed Nov. 2, 2009 now abandoned, the entire contents of which are hereby incorporated by reference.

BACKGROUND OF THE INVENTION

1. Field of the Invention

The present invention relates to a biological substance involved in insulin resistance, and more specifically, to an insulin resistance marker, a method of evaluating insulin resistance, a method of screening a substance that improves insulin resistance, and a pharmaceutical composition for improving insulin resistance. More specifically, the present invention relates to prevention of occurrence, diagnosis and therapy of insulin resistance and disease conditions and states accompanied with insulin resistance.

2. Disclosure of the Related Art

Now in Japan, the number of patients suffering from metabolic syndromes such as diabetes, hypertension, and hyperlipidemia that will cause severe adult diseases is dramatically increasing, and development of methods to prevent, diagnose and treat them is needed.

Since the major cause of a metabolic syndrome is obesity, various researches are undertaken to elucidate the mechanism of obesity. The 3T3-L1-strained cell derived from a mouse is one of the cells that are most frequently used in such researches as a model of an adipose tissue. A 3T3-L1 cell is proved to have a property that is well coincident with biochemical and physiological characteristics in an actual adipose tissue in such a meaning that by induction of differentiation, fat droplets are accumulated in the cell and uptake of extracellular glucose via an insulin receptor is promoted (Non-patent Document 1: Cell, Vol. 5, 19-27, May 1975).

As a research example using a 3T3-L1 cell, concretely, Patent Document 1: Japanese Patent Application Laid-Open Publication No. 2004-105175 reports on a protein and a gene secreted by an adipocyte, Patent Document 2: Japanese Patent Application Laid-Open Publication No. 2004-135605 reports on a protein and a gene involved in differentiation of an adipocyte, Patent Document 3: Japanese Patent Application Laid-Open Publication No. 2005-247740 reports on a protein having a function of controlling fatty acid metabolism that is expressed in the course of differentiation of an adipocyte, and Patent Document 4: Japanese Patent Application Laid-Open Publication No. 2006-141233 reports on a secreted protein and a gene involved in adipocyte hypertrophy.

3T3-L1 adipocytes are also used as an in vitro experimental model of human adipose tissues. For example, PPARγ (peroxisome proliferator-activated receptor γ), a key molecule for proliferation and differentiation of adipose cells, is known to have similar functions in 3T3-L1 adipocytes as well. Further, it was demonstrated that functions and expression patterns of many proteins in vitro experimental models were reflected in those in vivo such as mouse and human adipose tissues. Concrete examples of such a protein include adiponectin (Non-patent Document 2: Biochemical and Biophysical Research Communications 290, 1084-1089 (2002), Non-patent Document 3: NATURE MEDICINE, VOLUME 7, NUMBER 8, 941-936, AUGUST 2001, Patent Document 5: International Publication No. 2003/063394 pamphlet, Patent Document 6: International Publication No. 2004/061108 pamphlet), resistin (Non-patent Document 4: NATURE, VOL 409, 13, 292-293, JANUARY 2001, Non-patent Document 5: Biochemical and Biophysical Research Communications 288, 1027-1031 (2001), Patent Document 5, Patent Document 6), free fatty acid (Non-patent Document 6: THE JOURNAL OF BIOLOGICAL CHEMISTRY VOL. 280, NO. 42, pp. 35361-35371, Oct. 21, 2005), and visfatin (Non-patent Document 7: Biochemical and Biophysical Research Communications 359 (2007) 194-201) and the like.

Obesity, which results from adipocyte hypertrophy, is one of the primary risk factor of metabolic syndrome and insulin resistance in physiological and clinical implications. An adipose tissue is known as an important endocrine organ that regulates whole-body insulin sensitivity. Currently, a number of adipocytokines having an influence on differentiation and proliferation and hypertrophy of fat, and insulin sensitivity (for example, the aforementioned adiponectin, leptin, tumor necrosis factor α (TNFα) and so on) have been identified.

Insulin resistance is fundamental to the pathogenic factor of metabolic syndromes including type 2 diabetes mellitus. Therefore, it is expected that diagnosis and improvement of insulin resistance will lead to prevention and fundamental therapy of the lifestyle-related diseases including diabetes.

However, it is actually the case that a metabolic syndrome is detected by health examination or the like only after abnormality occurs in blood pressure or lipid metabolism following onset of insulin resistance. In other words, it is, in fact, very difficult to diagnose onset of insulin resistance in an early stage.

Therefore, discovery of a novel diagnostic marker capable of specifically detecting insulin resistance is demanded.

The aforementioned adipocytokines have not been brought into practical uses for therapy and diagnosis. On the other hand, as an insulin sensitizer for diabetes, thiazolidine-based drugs targeting an intranuclear receptor PPARγ are currently representative. Thiazolidine-based drugs have the effect of normalizing regulation of glycometabolism in the body by improving the insulin sensitivity. However, as for these drugs, problems such as side effects like hepatic dysfunction and necessity of strict drug administration control have been indicated.

Therefore, discovery of a novel drug target that shows a specific action on insulin resistance is demanded.

On the other hand, insulin resistance is known to be developed not only by environmental factors such as obesity and daily habits but also by various clinical factors such as pregnancy and long-term dosing of steroids. Although the reason why insulin resistance is induced due to such varied factors is not known, there is a report that these phenomena are also observed in in vivo and in vitro experiments. In other words, it was reported that a glucocorticoid (for example, dexamethasone) etc., in addition to an obesity-related factor (TNFα), induces insulin resistance of 3T3-L1 adipocytes (Non-patent Document 9: DIABETES, VOL. 49, 1700-1708, OCTOBER 2000, Non-patent Document 8: Proc. Natl. Acad. Sci. USA, Vol. 91, pp. 4854-4858, May 1994).

As for molecular mechanisms of insulin signal transduction, generalization has been widely made (Non-patent Document 10: Mol Cell Biochem 182, 31-48 (1998), Non-patent Document 11: Diabetes Metab 24, 477-89 (1998), Non-patent Document 12: Cell 92, 593-6 (1998), Non-patent Document 13: J Clin Invest 103, 931-43 (1999)).

Specifically, the interaction between insulin and insulin receptor results in activation of tyrosine kinase and phosphorylation of IRS-1. Then PI3-kinase (phosphoinositide 3-kinase), Grb2.Sos complex, and SHP-2 bind to the phosphorylated IRS-1. As a result, PI3-kinase is activated, and interacts with Akt (also referred to as PKB, protein kinase B). Akt is phosphorylated and activated by PDK1 (phosphatidylinositol-dependent protein kinase 1). The activated Akt is dissociated with the plasma membrane and phosphorylates various proteins. Therefore, in muscle cells (skeletal muscle, myocardium) and adipocytes, translocation of glucose transporters and GLUT4 (glucose transporter 4) containing vesicles are promoted. Thus, cellular uptake of glucose is promoted.

By the way, a proepithelin protein (also known as progranulin/PCDGF/PEPI/GEP/GP88) which is an epithelin precursor protein having seven kinds of epithelin domains is known. It is reported that proepithelin and epithelin have a growth factor-like function, and function as an autocrine growth factor as a result of being secreted outside the cell, and thus are involved in inflammation and cell migration (Non-patent Document 14: Journal of Molecular Medicine 81, 600-612 (2003)).

However, a relationship between such a protein or a peptide and insulin resistance is not known at all.

Patent Document 1: Japanese Patent Application Laid-Open Publication No. 2004-105175

Patent Document 2: Japanese Patent Application Laid-Open Publication No. 2004-135605

Patent Document 3: Japanese Patent Application Laid-Open Publication No. 2005-247740

Patent Document 4: Japanese Patent Application Laid-Open Publication No. 2006-141233

Patent Document 5: International Publication No. 2003/063894 pamphlet

Patent Document 6: International Publication No. 2004/061108 pamphlet

Non-patent Document 1: Cell, Vol. 5, 19-27, May 1975

Non-patent Document 2: Biochemical and Biophysical Research Communications 290, 1034-1089 (2002)

Non-patent Document 3: NATURE MEDICINE, VOLUME 7, NUMBER 8, 941-946, AUGUST 2001

Non-patent Document 4: NATURE, VOL 409, 18, 292-293, JANUARY 2001

Non-patent Document 5: Biochemical and Biophysical Research Communications 288, 1027-1031 (2001)

Non-patent Document 6: THE JOURNAL OF BIOLOGICAL CHEMISTRY VOL. 280, NO. 42, pp. 35361-35371, Oct. 21, 2005

Non-patent Document 7: Biochemical and Biophysical Research Communications 359 (2007) 194-201

Non-patent Document 8: Proc. Natl. Acad. Sci. USA, Vol. 91, pp. 4854-4858, May 1994

Non-patent Document 9: DIABETES, VOL. 49, 1700-1708, OCTOBER 2000

Non-patent Document 10: Mol Cell Biochem 182, 31-48 (1998)

Non-patent Document 11: Diabetes Metab 24, 477-89 (1998)

Non-patent Document 12: Cell 92, 593-6 (1998)

Non-patent Document 13: J Clin Invest 103, 931-43 (1999)

Non-patent Document 14: Journal of Molecular Medicine 81, 600-612 (2003)

SUMMARY OF THE INVENTION

It is an object of the present invention to provide a biological substance involved in insulin resistance, and a method of using the same. That is, it is an object of the present invention to provide an insulin resistance marker, a method of evaluating insulin resistance, a method of screening a substance that improves insulin resistance, and a pharmaceutical composition for improving insulin resistance.

Inventors of the present application performed analysis using matured adipocytes obtained by subjecting mouse preadipocytes (3T3-L1) to a differentiation treatment as a control group. The inventor searched for a protein that exhibits the expression variation that is common to an insulin resistant matured adipocyte. The insulin resistant matured adipocyte is obtained by inducing insulin resistance from the matured adipocyte of the control group with the use of an obesity-related factor TNFα and a glucocorticoid dexamethasone. As a result, as a protein exhibiting a significant expression increase commonly to these insulin resistant matured adipocytes, the present inventors identified proepithelin, a protein for which no relation with insulin resistance has been known heretofore.

The present invention includes the following aspects.

(1) An insulin resistance marker including a polypeptide comprising at least any 15 continuous amino acids in the amino acid sequence represented by SEQ ID NO: 1.

The "polypeptide" includes a polypeptide specified by a specific sequence (namely, any sequences made up of at least 15 continuous amino acids in the amino acid sequence represented by SEQ ID NO: 1), and polypeptides that are homology and mutants of said polypeptide having an equivalent biological function involved in insulin resistance to that of said polypeptide.

Therefore, the "polypeptide comprising at least any 15 continuous amino acids in the amino acid sequence represented by SEQ ID NO: 1" includes, as an example, a polypeptide made up of at least any 15 continuous amino acids in the amino acid sequence represented by SEQ ID NO: 3.

The "polypeptide" includes an oligopeptide and a protein.

The "insulin resistance" means the condition that a normal physiological or molecular response can not be induced by a normal amount of insulin. In some cases, it may include the condition that insulin resistance can be at least partly improved or a biological response can be induced by an excess physiological amount of insulin that is endogenously produced or externally added.

The "insulin resistance marker" means a marker for evaluating insulin resistance, and includes a marker that distinguishes a state accompanied with insulin resistance, and a marker that distinguishes a disease condition accompanied with insulin resistance.

(2) A method of evaluating insulin resistance, including the steps of:

measuring a level of a polypeptide comprising at least any 15 continuous amino acids in the amino acid sequence represented by SEQ ID NO: 1, in a sample derived from an individual which is an object of evaluation of insulin resistance, and comparing the obtained measured level with a normal level of the polypeptide, wherein an increase of the obtained measured level compared with the normal level is regarded as one index indicating that the objective individual has high possibility of being in the condition of insulin resistance.

"Evaluating insulin resistance" includes recognizing a state accompanied with insulin resistance, and recognizing a morbidity condition of a disease accompanied with insulin resistance, and more concretely, includes conducting detection and diagnosis of insulin resistance, and detection, diagnosis, monitoring, staging and determination of prognosis of a disease accompanied with insulin resistance.

The "individual" includes any animals. For example, mammals such as primates (e.g., human being), rodents (e.g., mouse and rat), rabbit, dog, cat, pig, bovine, sheep and horse may be recited.

The term "level" includes an expression level and a secretion level.

(3) A method of screening a substance for improving insulin resistance, including the steps of:

bringing a sample containing a polypeptide comprising at least any 15 continuous amino acids in the amino acid sequence represented by SEQ ID NO: 1, or a cell capable of expressing or secreting the polypeptide, into contact with a candidate substance;

measuring a level of the polypeptide or an expression level or a secretion level of the polypeptide in the cell when the candidate substance is brought into contact, and comparing the measured level of the polypeptide or the measured expression level or the measured secretion level of the polypeptide in the cell when the candidate substance is brought into contact, with a level of the polypeptide or an expression level or a secretion level of the polypeptide in the cell when the candidate substance is not brought into contact, wherein a reduction of the measured level, the measured expression level or the measured secretion level when the candidate substance is brought into contact, compared with the level, the expression level or the secretion level when the candidate substance is not brought into contact, is regarded as one index for selecting the candidate substance as a substance that improves insulin resistance.

"Improving insulin resistance" includes converting insulin resistance into higher insulin sensitivity, and converting insulin resistance into a higher glucose transport activity, and more concretely, includes controlling an insulin signaling-suppressing action in insulin resistance and controlling a glucose transport system-suppressing action, and curing a disease accompanied with insulin resistance may be recited as an example.

By controlling expression of the insulin resistance marker of the present invention by the method of the above (3), it is possible to select a substance that improves insulin resistance.

(4) A method of screening a substance that improves insulin resistance, including the steps of:

bringing a sample containing a polypeptide comprising at least any 15 continuous amino acids in the amino acid sequence represented by SEQ ID NO: 1, or a cell that expresses or secretes the polypeptide, into contact with a candidate substance;

measuring a function of the polypeptide or a function of the polypeptide in the cell when the candidate substance is brought into contact, and comparing the measured function of the polypeptide or the measured function of the polypeptide in the cell when the candidate substance is brought into contact, with the function of the polypeptide or the function of the polypeptide in the cell when the candidate substance is not brought into contact, wherein the measured function when the candidate substance is brought into contact being more controlled compared with the function when the candidate substance is not brought into contact, is regarded as one index for selecting the candidate substance as a substance that improves insulin resistance.

The "function" includes an insulin resistance-inducing activity.

By controlling the insulin resistance-inducing activity (for example, an insulin signaling-suppressing activity) by the insulin resistance marker of the present invention according to the method of the above (4), it is possible to select a substance that improves insulin resistance.

The method according to the above (4), wherein the measurement of the function of the polypeptide is conducted by measuring a level of an insulin signaling-related factor selected from the group consisting of Akt, phosphorylated Akt and factors that function downstream the Akt in the insulin signaling pathway, and a reduction or an increase of the measured level of the insulin signaling-related factor when the candidate substance is brought into contact, compared with a level of the insulin signaling-related factor when the candidate substance is not brought into contact, is regarded as one index for selecting the candidate substance as a substance that improves insulin resistance.

The "Akt" is a serine/threonine kinase which is also called PKB or protein kinase B.

The "factors that function downstream the Akt in the insulin signaling pathway" refer to factors that are involved in a series of routes in the insulin signaling pathway from undergoing activation by phsphorylated Akt to uptaking glucose into a cell (namely, a glucose transport system).

(5) A pharmaceutical composition for improving insulin resistance including a polypeptide comprising at least any 15 continuous amino acids in the amino acid sequence represented by SEQ ID NO: 1.

(6) A pharmaceutical composition for improving insulin resistance including an antibody against a polypeptide comprising at least any 15 continuous amino acids in the amino acid sequence represented by SEQ ID NO: 1.

The "antibody" includes a polyclonal antibody, a monoclonal antibody, and antibodies prepared by molecular biological techniques.

The "antibody" widely means a substance that binds in an immune-specific manner, and includes antibody fragments and antibody-fused proteins.

(7) A pharmaceutical composition for improving insulin resistance including a substance that controls an expression level or a secretion level of a polypeptide comprising at least any 15 continuous amino acids in the amino acid sequence represented by SEQ ID NO: 1, as an active ingredient.

(8) A pharmaceutical composition for improving insulin resistance including a substance that controls a function by a polypeptide comprising at least any 15 continuous amino acids in the amino acid sequence represented by SEQ ID NO: 1, as an active ingredient.

A pharmaceutical composition for improving insulin resistance including a substance that upregulates an insulin signaling-related factor that is downregulated by expression of a polypeptide comprising at least any 15 continuous amino acids in the amino acid sequence represented by SEQ ID NO: 1, as an active ingredient.

(9) An insulin resistance marker including a polynucleotide selected from the group consisting of a polynucleotide comprising at least any 45 continuous bases in the base sequence represented by SEQ ID NO: 2 and a polynucleotide that is complementary to the polynucleotide.

The "base sequence represented by SEQ ID NO: 2" is a base sequence that encodes the amino acid sequence represented by SEQ ID NO.1.

The "polynucleotide" includes polynucleotide specified by a specific sequence (namely, a sequence comprising at least any 45 continuous bases in the base sequence represented by SEQ ID NO: 2), and polynucleotides encoding polypeptides that are homologs and mutants of a polypeptide encoded by the polynucleotide and have an equivalent biological function involved in insulin resistance to that of the polypeptide.

Therefore, the "polynucleotide selected from the group consisting of a polynucleotide comprising at least any 45 continuous bases in the base sequence represented by SEQ ID NO: 2 and a polynucleotide that is complementary to the polynucleotide" includes, as one example, a polynucleotide selected from the group consisting of a polynucleotide comprising at least any 45 continuous bases in the base sequence represented by SEQ ID NO: 4 and a polynucleotide complementary to the polynucleotide.

The "polynucleotide" includes an oligopeptide and a polynucleotide.

The "polynucleotide" includes a DNA and an RNA. The DNA includes cDNA, genomic DNA, and synthetic DNA. The RNA includes total RNA, mRNA, rRNA, and synthetic RNA.

The "polynucleotide" includes a single-stranded polynucleotide and a double-stranded polynucleotide.

(10) A method of evaluating insulin resistance, including the steps of:

measuring a level of a polynucleotide selected from the group consisting of a polynucleotide comprising at least any 45 continuous bases in the base sequence represented by SEQ ID NO: 2 and a polynucleotide complementary to the polynucleotide, in a sample derived from an individual which is an object of evaluation of insulin resistance, and comparing the obtained measured level with a normal level of the polynucleotide, wherein an increase of the obtained measured level compared with the normal level is regarded as one index indicating that the objective individual has high possibility of being in the condition of insulin resistance.

(11) A method of screening a substance for improving insulin resistance, including the steps of:

bringing a sample containing a polynucleotide selected from the group consisting of a polynucleotide comprising at least any 45 continuous bases in the base sequence represented by SEQ ID NO: 2 and a polynucleotide complementary to the polynucleotide, or a cell capable of expressing the polynucleotide, into contact with a candidate substance;

measuring a level of the polynucleotide or an expression level of the polynucleotide in the cell when the candidate substance is brought into contact, and comparing the measured level of the polynucleotide or the measured expression level of the polynucleotide in the cell when the candidate substance is brought into contact, with a level of the polynucleotide or an expression level of the polynucleotide in the cell when the candidate substance is not brought into contact, wherein a reduction of the measured level or the measured expression level when the candidate substance is brought into contact, compared with the level or the expression level when the candidate substance is not brought into contact, is regarded as one index for selecting the candidate substance as a substance that improves insulin resistance.

The candidate substance selected by the above method (11) is a substance capable of controlling expression of a polynucleotide which is an insulin resistance marker of the present invention.

(12) A pharmaceutical composition for improving insulin resistance including a polynucleotide selected from the group consisting of a polynucleotide comprising at least any 45 continuous bases in the base sequence represented by SEQ ID NO: 2 and a polynucleotide complementary to the polynucleotide.

(13) A pharmaceutical composition for improving insulin resistance including a substance that controls an expression level of a polynucleotide selected from the group consisting of a polynucleotide comprising at least any 45 continuous bases in the base sequence represented by SEQ ID NO: 2 and a polynucleotide complementary to the polynucleotide, as an active ingredient.

According to the present invention, it is possible to provide an insulin resistance marker, a method of evaluating insulin resistance, a method of screening a substance that improves insulin resistance, and a pharmaceutical composition for improving insulin resistance. The present invention makes it possible to achieve prevention of onset, diagnosis and therapy of insulin resistance and a disease condition and a state accompanied with insulin resistance.

DETAILED DESCRIPTION OF THE INVENTION

1. Insulin Resistance Marker

Figure 1:
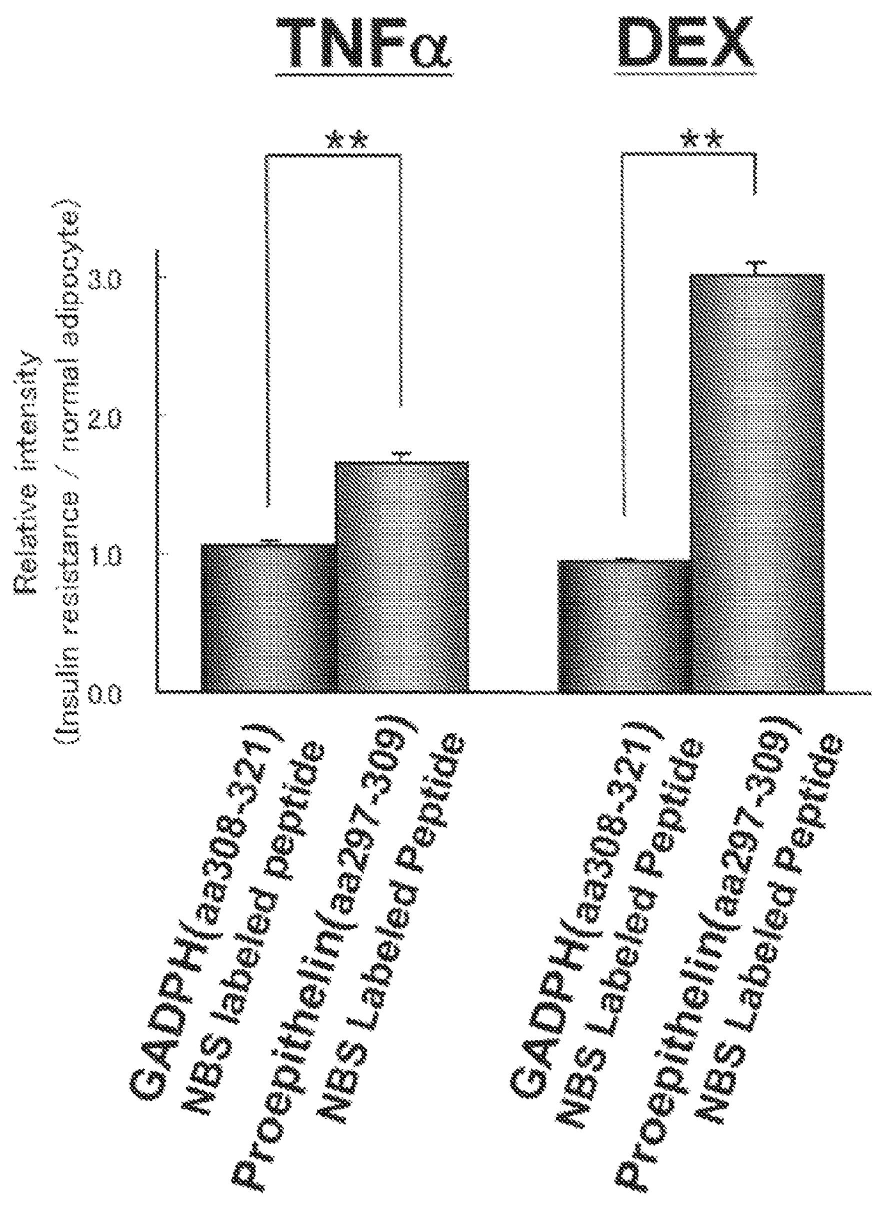
FIG. 1 shows a result of analysis of expression variation of a proepithelin protein by the NBS method.

"Insulin resistance" refers to the condition that a normal physiological or molecular response cannot be caused by a normal amount of insulin. Occasionally, it may include the condition that insulin resistance can be at least partly improved or a biological response can be caused by an excess physiological amount of insulin that is endogenously produced or exogenously added.

Here, a concrete definition of the "normal amount" is appropriately made by a person skilled in the art. For example, in the case of an adult person, fasting blood insulin (IRI value) is 10 μU/mL or less. However, the normal amount is defined by various other factors without limited to this.

Also the quantitative definition of "insulin resistance" is appropriately made by a person skilled in the art. For example, it is often the case that deviation from 2.5 or less, which is a normal value of HOMA-R value, is diagnosed to be suspected of insulin resistance. However, the quantitative definition of insulin resistance may be made by other factors without limited to this.

The present invention is based on the finding that a protein having the amino acid sequence of SEQ ID NO: 3 exhibits a significant upregulation in a model of insulin resistance.

As a model of insulin resistance, an insulin resistant matured adipocyte obtained by inducing insulin resistance using TNFα from a matured adipocyte that was obtained by subjecting a mouse preadipocyte (3T3-L1) to a differentiation treatment, and an insulin resistant matured adipocyte obtained by inducing insulin resistance using a glucocorticoid dexamethasone, are both used. Using a matured adipocyte obtained by subjecting a mouse preadipocyte (3T3-L1)

to a differentiation treatment, in which insulin resistance is not induced, as a control group, proepithelin having the amino acid sequence represented by SEQ ID NO: 3 was identified as a protein that exhibits a significant upregulation ($p<0.05$) in both models commonly.

Here, while both of stimulation by TNFα which is an obesity-related factor and stimulation by dexamethasone which is a glucocorticoid having little relation with obesity will cause insulin resistance, they cause insulin resistance via individual mechanisms which are largely different from each other. Specifically, TNFα is mediated by a cytokine receptor on cell surface, while dexamethasone is mediated by a nuclear hormone receptor. The protein of the present invention exhibiting a common expression variation for insulin resistance inducing factors that are mediated by largely different mechanisms is effectively used as the one that strongly suggests direct relation with insulin resistance, namely as an insulin resistance marker.

Therefore, in addition to a protein having the amino acid sequence represented by SEQ ID NO: 3, a human homologue of a protein having the amino acid sequence represented by SEQ ID NO: 3 (namely, a protein having the amino acid sequence represented by SEQ ID NO: 1), a polynucleotide encoding a protein having the amino acid sequence represented by SEQ ID NO: 3 (namely, a polynucleotide represented by SEQ ID NO: 4), and a polynucleotide encoding a protein having the amino acid sequence represented by SEQ ID NO: 1 (namely, a polynucleotide represented by SEQ ID NO: 2) are also used usefully as insulin resistance markers.

The term "insulin resistance marker" refers to a marker for evaluation of insulin resistance, and includes a marker recognizing a state accompanied with insulin resistance, and a marker recognizing a morbidity condition of a disease accompanied with insulin resistance.

Examples of the state and the morbidity condition of a disease accompanied with insulin resistance include type 2 diabetes mellitus, metabolic syndromes, prediabetes, polycystic ovary syndrome, abnormal lipid metabolism, obesity, sterility, inflammatory abnormality, cancer, inflammatory disease, Alzheimer's disease, high blood pressure, atherosclerosis, cardiovascular disease, and peripheral vascular disease.

1-1. Polypeptide

The present invention is an insulin resistance marker including a polypeptide comprising at least any 15 continuous amino acids in the amino acid sequence represented by SEQ ID NO: 1.

The "polypeptide" includes an oligopeptide and a protein.

The "amino acid sequence represented by SEQ ID NO: 1" is a sequence of a human homologue of proepithelin.

The "polypeptide comprising at least any 15 continuous amino acids in the amino acid sequence represented by SEQ ID NO: 1" includes proepithelin, epithelin peptides (concretely, 1-epithelin, 2-epithelin, 3-epithelin, 4-epithelin, 5-epithelin, 6-epithelin, and 7-epithelin), and any polypeptides containing partially or entirely a minimum sequence involved in insulin resistance in a proepithelin sequence.

The polypeptide comprising at least any 15 continuous amino acids in the amino acid sequence represented by SEQ ID NO: 1 may be a polypeptide comprising at least any 50 continuous amino acids in the sequence, or may be a polypeptide comprising at least any 593 continuous amino acids in the sequence.

The "polypeptide comprising at least any 15 continuous amino acids in the amino acid sequence represented by SEQ ID NO: 1" also includes a polypeptide specified by a sequence comprising at least any 15 continuous amino acids in the amino acid sequence represented by SEQ ID NO: 1, and polypeptides that are homologs and mutants of the polypeptide having an equivalent biological function involved in insulin resistance to that of the polypeptide.

The homologs include an entire or partial sequence of a homolog of mouse, rat and other species corresponding to a human homolog of proepithelin.

Therefore, the "polypeptide comprising at least any 15 continuous amino acids in the amino acid sequence represented by SEQ ID NO: 1" includes a "polypeptide comprising at least any 15 continuous amino acids in the amino acid sequence represented by SEQ ID NO: 3" which is a mouse homolog.

The mutants include naturally occurring mutants of proepithelin, and mutants modified by artificial replacement, addition, insertion and deletion of an amino acid.

These homologs and mutants have a homology of at least 80%, preferably at least 85%, more preferably at least 90%, and further preferably at least 95% with the sequence comprising at least any 15 continuous amino acids in the amino acid sequence represented by SEQ ID NO: 1.

For example, it is well known that mouse and human have a homology of 84% or more in an amino acid level. As for the metabolic mechanism and the signal transduction mechanism that bear the fundamentals of life, it is generally recognized that these mechanisms are extremely similar between mouse and human, and in fact, those exhibiting similar functions and expression variations between an adipocyte of mouse and an adipocyte of human have been frequently reported. Therefore, it is clear that there is no exception in glycometabolism regulation or in insulin signal transduction. It is generally recognized by a person skilled in the art that glycometabolism regulation and insulin signal transduction may be common mechanisms among the entire mammals including mouse and human with very high possibility. Therefore, it is extremely reasonable that the polynucleotide in the present invention includes those basically having a sequence comprising at least any 15 continuous amino acids in the amino acid sequence represented by SEQ ID NO: 1 and having a homology of at least 80%. For example, a mouse homolog represented by SEQ ID NO: 3 is 84% homologous (by BLAST homology search) with a human homolog represented by SEQ ID NO: 1.

1-2. Polynucleotide

The present invention provides an insulin resistance marker including a polynucleotide selected from the group consisting of a polynucleotide comprising at least any 45 continuous bases in the base sequence represented by SEQ ID NO: 2 and a polynucleotide complementary to the polynucleotide.

The "polynucleotide" includes an oligopeptide and a polynucleotide. The "polynucleotide" includes a DNA and an RNA. The DNA includes cDNA, genomic DNA, and synthetic DNA. The RNA includes total RNA, mRNA, rRNA, and synthetic RNA. Further the term "polynucleotide" includes a single-stranded polynucleotide and a double-stranded polynucleotide.

The "base sequence represented by SEQ ID NO: 2" is a base sequence that encodes the polypeptide represented by SEQ ID NO: 1, namely a base sequence that encodes a human homolog of proepithelin.

The "polynucleotide comprising at least any 45 continuous bases in the base sequence represented by SEQ ID NO: 2" includes polynucleotides that encode proepithelin, epithelin peptides (concretely, 1-epithelin, 2-epithelin, 3-epithelin, 4-epithelin, 5-epithelin, 6-epithelin, and 7-epithelin), and any polypeptides containing partially or entirely a minimum sequence involved in insulin resistance in the sequence of proepithelin.

The polynucleotide comprising at least any 45 continuous bases in the base sequence represented by SEQ ID NO: 2 may be a polypeptide comprising at least any 150 continuous amino acids in the sequence, or a polypeptide comprising at least any 1779 continuous amino acids in the sequence.

The "polynucleotide comprising at least any 45 continuous bases in the base sequence represented by SEQ ID NO: 2" includes a polynucleotide specified by a sequence comprising at least any 45 continuous bases in the base sequence represented by SEQ ID NO: 2 and polynucleotides encoding polypeptides that are homologs and mutants of the polypeptide encoded by the polynucleotide and have an equivalent biological function involved in insulin resistance to that of the polypeptide.

The polynucleotides encoding homologs include the entire or partial sequences of homologs of mouse, rat and other species, corresponding to a human homolog of a polynucleotide encoding proepithelin.

Therefore, the "polynucleotide selected from the group consisting of a polynucleotide comprising at least any 45 continuous bases in the base sequence represented by SEQ ID NO: 2 and a polynucleotide complementary to the polynucleotide" includes a polynucleotide selected from the group consisting of a polynucleotide comprising at least any 45 continuous bases in the base sequence represented by SEQ ID NO: 4 which is a mouse homolog and a polynucleotide which is complementary to the polynucleotide.

The polynucleotides encoding the mutants include naturally occurring mutants, and mutants modified by artificial replacement, addition, insertion and deletion of a base of a polynucleotide encoding proepithelin.

These polynucleotides encoding homologs and mutants have a homology of at least 80%, preferably at least 85%, more preferably at least 90%, and further preferably at least 95% with a sequence comprising at least any 45 continuous bases in the base sequence of SEQ ID NO: 2.

2. Method of Evaluating Insulin Resistance

The aforementioned insulin resistance marker of the present invention is useful in a method of evaluating insulin resistance. The present invention provides a method of evaluating insulin resistance by using the aforementioned insulin resistance marker.

"Evaluating insulin resistance" includes identifying a state accompanied with insulin resistance and identifying a morbidity condition of a disease accompanied with insulin resistance, and more specifically conducting detection and diagnosis of insulin resistance, and detection, diagnosis, monitoring, staging and prognosis determination of a disease accompanied with insulin resistance. Determination of prognosis includes determining presence or absence or the degree of improvement of the disease after a therapy when the therapy for improving the disease is conducted.

The method of evaluating insulin resistance of the present invention includes the following steps:

measuring a level of an insulin resistance marker in a sample derived from an individual which is an object of evaluation of insulin resistance, and comparing the obtained measured level with a normal level of the insulin resistance marker, wherein an increase of the obtained measured level compared with the normal level is regarded as one index indicating that the objective individual has high possibility of being in the condition of insulin resistance.

In the method of the present invention, the insulin resistance marker of the present invention may be measured alone, or measured in combination with any other marker related with a state or a disease condition of insulin resistance. Therefore, the method of the present invention may include measuring a level of another marker likewise the level of the insulin resistance marker of the present invention.

In the present invention, a sample derived from an individual which is an object of evaluation of insulin resistance is not particularly limited. For example, cells, tissues, bodily fluids, and extracts thereof and the like may be recited. Cells and tissues include tissue biopsy materials and autopsy materials and the like. Bodily fluids include blood, bodily secretions and on the like. As blood, whole blood, plasma, serum and on the like are included. The term tissue extract refers to a cell or a tissue homogenized or solubilized by a method known to a person skilled in the art. Among these exemplified samples, it is preferred to use an extract of an adipose tissue or an adipocyte as a sample.

The "individual" includes every animal. For example, mammals such as primates (e.g., human being), rodents (e.g., mouse and rat), rabbit, dog, cat, pig, bovine, sheep and horse may be recited.

The "level" includes an expression level and a secretion level.

The "normal level" includes a level in a normal sample. As a normal sample, cells, tissues, bodily fluids and extracts thereof, and preferably, an extract of an adipose tissue or an adipocyte, which have insulin sensitivity, may be recited.

Insulin sensitivity refers to the condition capable of causing a normal physiological or molecular response by a normal amount of insulin.

Here, a concrete definition of the normal amount is appropriately made by a person skilled in the art. For example, in the case of an adult person, fasting blood insulin (IRI value) is 10 μU/mL or less. However, the normal amount is also defined by various other factors without limited to this.

Also the quantitative definition of insulin sensitivity is appropriately made by a person skilled in the art. For example, it is often the case that 2.5 or less, which is a normal value of HOMA-R value, is diagnosed to be insulin sensitive. However, the quantitative definition of insulin sensitivity may be made by other factors without limited to this.

The degree of increase in measured level is not particularly limited because it differs depending on a measurement method and the like, however, for example, the degree in which the measured level is 1.25 times or more, preferably 1.5 times or more, and more preferably twice or more (molar base) the normal level may be regarded as a criterion.

2-1. The Case Based on Level of Polypeptide

Concretely, a mouse homolog of a polypeptide having the amino acid sequence represented by SEQ ID NO: 1 showed a specific increase in expression amount in a matured cell of a 3T3-L1 cell which can be a model of a state or a disease condition accompanied with insulin resistance. Therefore, when a polypeptide comprising at least any 15 continuous amino acids in the amino acid sequence represented by SEQ ID NO: 1 specifically increases (for example, increases to 1.25 times or more, preferably 1.5 times or mere, and more preferably twice or more (molar base) the normal level) in a sample derived from an individual which is an object of evaluation of insulin resistance, a state or a disease condition of insulin resistance can be suspected.

A method of measuring a level of a polypeptide is not particularly limited, and any method capable of specifically detecting a specific polypeptide may be used. Preferably, the level is measured by a test based on biospecific affinity. The test based on biospecific affinity is well known to a person skilled in the art, and immunoassay is preferable without particularly limited thereto. Concretely, immunoassays such as Western blotting, radio immunoassay, ELISA, sandwich immunoassay, immunoprecipitation, precipitation reaction, gel diffusion precipitin reaction, immunodiffusion, agglutination measurement, complement fixation analysis assay, immunoradiometric assay, fluorescent immunoassay, and protein A immunoassay including a competitive or noncompetitive assay system may be recited. In these methods, existence of an antibody that binds to the insulin resistance marker in a sample of an individual is detected. Concretely, the test is conducted by bringing a sample into contact with the antibody in the condition that an immune complex made up of a tumor marker polypeptide to be measured and an antibody of the polypeptide can be formed in an assay medium, or on a tissue section. A more concrete protocol may be readily determined by a person skilled in the art.

The level of a polypeptide is preferably measured by a test based on biospecific affinity as described above, however, it may be measured by other quantification methods. For example, an isotope labeling method is an excellent quantification method. In this case, by examining a difference in abundance of the polypeptide between a control sample which is a sample prepared to contain a known level of the polypeptide or an appropriate sample such as a normal sample, and a sample of an objective individual, it is possible to achieve measurement.

2-2. The Case Based on Level of Polynucleotide

Concretely, a mouse homolog of a polypeptide having the amino acid sequence represented by SEQ ID NO: 1 showed a specific increase in expression amount in a matured cell of a 3TL3-L1 cell which can be a model of a state or a disease condition accompanied with insulin resistance. Therefore, when a polynucleotide selected from the group consisting of the polynucleotide comprising at least any 45 continuous bases in the base sequence represented by SEQ ID NO: 2 encoding the amino acid sequence of SEQ ID NO: 1 and a polynucleotide complementary to the polynucleotide specifically increases in a sample derived from an individual which is an object of evaluation of insulin resistance (for example, increases to 1.25 times or more, preferably 1.5 times or more, and more preferably twice or more (molar base) the normal level), a state or a disease condition of insulin resistance is suspected.

As a method of measuring a level of a polynucleotide, any method capable of specifically detecting a specific polynucleotide may be used without any particular limitation. For example, the Northern blotting method, RT-PCR method, DNA chip analysis, in situ hybridization and the like may be used. These methods are well known to a person skilled in the art.

3. Method of Screening Substance That Improves Insulin Resistance

The aforementioned insulin resistance marker of the present invention is useful in a method of screening a substance that improves insulin resistance. Accordingly, the present invention provides a method of screening a substance that improves insulin resistance by controlling expression of the insulin resistance marker of the present invention, or by controlling the function of the insulin resistance marker of the present invention (concretely, an insulin resistance-inducing activity, for example, an insulin signaling-suppressing activity).

The candidate substance thus obtained is useful as an active ingredient of a pharmaceutical composition for improving insulin resistance.

"Improving insulin resistance" includes changing insulin resistance into higher insulin sensitivity, and changing insulin resistance into a higher glucose transport activity, and more concretely, controlling the action of suppressing insulin signal transduction in insulin resistance, and controlling a glucose transport system-suppressing action, and for example, treating a disease accompanied with insulin resistance.

Examples of possible candidate substances include, but are not limited to, a nucleic acid, a protein, a peptide, an organic compound, an inorganic compound and so on. Examples of a sample that contains such a candidate substance include, but are not limited to, a cell extract, an expression product of a polynucleotide library, a synthetic compound having low molecular weight, a synthetic peptide, a natural compound, and a mixture thereof and the like.

3-1. The Case Based on Level of Insulin Resistance Marker (Polypeptide or Polynucleotide)

This method is a method of screening an insulin resistance improving substance that controls expression of an insulin resistance marker, and utilizes the fact that an increase in the level of an insulin resistance marker is related with a state or a disease condition of insulin resistance.

Therefore, in screening of a candidate substance that improves insulin resistance, variation in expression of the insulin resistance marker of the present invention will be one index.

The method of screening a substance that improves insulin resistance based on an expression amount of an insulin resistance marker includes the following steps:

bringing an insulin resistance sample into contact with a candidate substance;

measuring a level of an insulin resistance marker in the insulin resistance sample when it is brought into contact with the candidate substance, and comparing the measured level of the insulin resistance marker when the candidate substance is brought into contact, with a level of the insulin resistance marker when the candidate substance is not brought into contact, wherein a reduction of the level of the insulin resistance marker when the candidate substance is brought into contact, compared with the level of the insulin resistance marker when the candidate substance is not brought into contact, is used as one index for selecting the candidate substance as a substance that improves insulin resistance.

The degree of reduction of the measured insulin resistance marker level is not particularly limited because it differs depending on the measuring method or the like, however, it is preferred to reduce to the level near the normal level, or to the normal level from the view point of curing the insulin resistance.

The "normal level" may be a level in a normal cell. The term normal cell means a cell having insulin sensitivity. Insulin sensitivity means the condition that causes a normal physiological or molecular response by a normal amount of insulin.

Here, a concrete definition of the normal amount is appropriately made by a person skilled in the art. For example, in the case of an adult person, fasting blood insulin (IRI value) is 10 μU/mL or less. However, the normal amount may be defined by various other factors without limited to this.

Also the quantitative definition of insulin sensitivity is appropriately made by a person skilled in the art. For example, it is often the case that 2.5 or less, which is a normal value of HOMA-R value, is diagnosed to be insulin sensitive. However, the quantitative definition of insulin sensitivity may be made by other factors without limited to this.

As a concrete degree of reduction in the level of the measured insulin resistance marker, for example, the degree of $1/1.25$ or less, preferably $1/1.5$ or less, and more preferably ½ or less (molar base) of the measured level of the insulin resistance marker may be regarded as a standard.

An index for selecting a candidate substance may be based solely on a level of the insulin resistance marker of the present invention, or may be based on a combination with any other marker information related with a state or a disease condition of insulin resistance. Therefore, the method of the present invention may use a combination of a sample related with the other marker as well as the insulin resistance sample related with the insulin resistance marker of the present invention.

As an insulin resistance sample used for screening, a sample containing an insulin resistance marker, and a cell having an ability to express or secrete the insulin resistance marker may be recited.

As an insulin resistance sample used in screening according to an expression amount of a polynucleotide as an index, the following samples may be recited.

As a sample containing an insulin resistance marker used in screening, an aqueous solution or cell (for example, later-described cell)-derived fraction containing a polynucleotide selected from the group consisting of a polynucleotide containing at least any 45 continuous bases in the base sequence represented by SEQ ID NO: 2 and a polynucleotide complementary to the polynucleotide may be recited.

For example, a cell lysate, a cell homogenate, and a nuclear extract containing the polynucleotide may be recited.

As a cell capable of expressing an insulin resistance marker used in screening, cells which may be endogenous or exogenous, capable of expressing a polynucleotide selected from the group consisting of the polynucleotide comprising at least any 45 continuous bases in the base sequence represented by SEQ ID NO: 2 and a polynucleotide complementary to the polynucleotide may be recited.

For example, a cell endogenously expressing the polynucleotide may be used. As such a cell, for example, mouse cells (3T3-L1, NIH3T3 and so on), and human cells (A431, MCF-7 and so on) may be recited.

For example, a transgenic cell into which the above polynucleotide is introduced may be used. As a host cell used for transgenesis, for example, cells derived from mouse (NIH 3T3, C127, COP, MOP, WOP and so on), cells derived from hamster (CHO, CHO DHFR- and so on), cells derived from monkey (COS-7, COS-1, CV-1 and so on), cells derived from human (HeLa and so on), and cells derived from insects (Sf21, Sf9, High Five and so on) may be recited.

As an insulin resistance sample that is used in conducting screening using an expression amount of a polypeptide as an index, the following samples may be used.

As a sample containing an insulin resistance marker used for screening, an aqueous solution or cell (for example, later-described cell)-derived fraction containing a polypeptide comprising at least any 15 continuous amino acids in the amino acid sequence represented by SEQ ID NO: 1 may be recited.

For example, a cell lysate, a cell homogenate, and a nuclear extract containing the polypeptide may be recited.

As a cell capable of expressing an insulin resistance marker used in screening, a cell capable of expressing a polypeptide comprising at least any 15 continuous amino acids in the amino acid sequence represented by SEQ ID NO: 1 may be recited.

That is, there may be recited cells which may be endogenous or exogenous, capable of expressing a polynucleotide selected from the group consisting of a polynucleotide comprising at least any 45 continuous bases in the base sequence represented by SEQ ID NO: 2 and a polynucleotide complementary to the polynucleotide, and expressing a polypeptide comprising at least any 15 continuous amino acids in the amino acid sequence represented by SEQ ID NO: 1 as a translation product.

As such a cell, as described in the case of conducting screening based on an expression amount of a polynucleotide as an index, a cell endogenously expressing the polynucleotide or a cell into which the polynucleotide is introduced may be used.

In the method of the present invention, the cell used in screening also includes a tissue which is an assembly of cells.

A condition at the time of bringing a candidate substance into contact with a cell is not particularly limited, and a person skilled in the art will appropriately determine culture conditions (culture medium composition, temperature, pH and the like) that enable expression of the insulin resistance marker (the aforementioned polynucleotide or the aforementioned polypeptide).

Selection of a substance that controls an expression amount of the insulin resistance marker of the present invention may be achieved in the following manner.

For example, a substance may be selected based on a reduction in a level of the insulin resistance marker in a sample with which the candidate substance is brought into contact, compared with a level of the insulin resistance marker in a sample with which the candidate substance is not brought into contact with the candidate substance, or a reduction in an expression level or a secretion level of the insulin resistance marker in a cell brought into contact with the candidate substance, compared with an expression level or a secretion level of the insulin resistance marker in a cell not brought into contact with the candidate substance, as an index.

For example, when using a cell that requires an expression inducing substance (for example, TNFα, a glucocorticoid (dexamethasone), a free fatty acid, resistin, PAI-1) for expression of the insulin resistance marker, a substance may be selected based on a reduction in the level of the insulin resistance marker in a cell brought into contact with the candidate substance in the presence of the expression inducing substance, compared with the level of the insulin resistance marker in a cell not brought into contact with the candidate substance in the presence of the expression inducing substance, as an index.

3-2. The Case Based on Function (Activity) of Polypeptide

This method utilizes the fact that constant presence of an insulin resistance marker inhibits insulin signal transduction, namely, is related with a state or a disease condition of insulin resistance.

Therefore, in screening of a candidate substance that improves insulin resistance, variation in function (concretely, an insulin resistance-inducing activity due to constant presence of the insulin resistance marker, for example, an activity of suppressing the insulin signaling pathway due to constant presence of the insulin resistance marker) of the insulin resistance marker of the present invention will be one index.

A method of screening a substance that improves insulin resistance based on the function (activity) of a polypeptide includes the following steps:

bringing a sample that is constantly insulin resistant into contact with a candidate substance;

measuring a function of an insulin resistance marker in the insulin resistance sample that is brought into contact with the candidate substance, and comparing the measured function of the polypeptide or the measured function of the polypeptide in the cell when the candidate substance is brought into contact, with the function of the polypeptide or the function of the polypeptide in the cell when the candidate substance is not brought into contact, wherein suppression of the measured function of the insulin resistance marker when the candidate substance is brought into contact, compared with the function of the insulin resistance marker when the candidate substance is not brought into contact, is regarded as one index for selecting the candidate substance as a substance that improves insulin resistance.

An index for selecting a candidate substance may be based solely on the function of the insulin resistance marker of the present invention, or may be combined with information of any other marker that is related with a state or a disease condition of insulin resistance. Therefore, the method of the present invention may use a combination of a sample related with the other marker as well as the insulin resistance sample related with the insulin resistance marker of the present invention.

As an insulin resistance sample used for screening, a sample in which an insulin resistance marker is constantly present is used, and concretely, a sample which is exposed to the insulin resistance marker for a long term, and a cell in which the insulin resistance marker is constantly expressed or secreted may be recited.

As the sample or cell, basically, those similar to those used in the case based on the level of the insulin resistance marker (polypeptide) as described above may be used.

Therefore, as a sample containing an insulin resistance marker used in screening, an aqueous solution or cell (for example, later-described cell)-derived fraction containing a polypeptide comprising at least any 15 continuous amino acids in the amino acid sequence represented by SEQ ID NO: 1 and the like may be recited.

For example, a cell lysate, a cell homogenate, and a nuclear extract containing the polypeptide may be recited.

As a cell capable of expressing or secreting an insulin resistance marker used in screening, a cell capable of expressing or secreting a polypeptide comprising at least any 15 continuous amino acids in the amino acid sequence represented by SEQ ID NO: 1 may be recited.

That is, there may be recited cells which may be endogenous or exogenous, capable of expressing a polynucleotide selected from the group consisting of a polynucleotide comprising at least any 45 continuous bases in the base sequence represented by SEQ ID NO: 2 and a polynucleotide complementary to the polynucleotide, and expressing or secreting a polypeptide comprising at least any 15 continuous amino acids in the amino acid sequence represented by SEQ ID NO: 1 as a translation product.

As such a cell, a cell endogenously expressing the polynucleotide may be used. As such a cell, for example, mouse cells (3T3-L1, NIH3T3 and so on), and human cells (A431, MCF-7 and so on) may be recited.

For example, a transgenic cell into which the above polynucleotide is introduced may be used. As a host cell used for transgenesis, for example, cells derived from mouse (NIH 3T3, C127, COP, MOP, WOP and so on), cells derived from hamster (CHO, CHO DHFR- and so on), cells derived from monkey (COS-7, COS-1, CV-1 and so on), cells derived from human (HeLa and so on), and cells derived from insects (Sf21, Sf9, High Five and so on) may be recited.

The cell used in screening also includes a tissue which is an assembly of cells.

Further, it is possible to require that a sample used in screening is exposed to an insulin resistance marker for a long term, or it constantly expresses or secrets an insulin resistance marker. The terms long term and constant used herein may be at least 4 hours, and preferably at least 16 hours.

The condition at the time of bringing a candidate substance into contact with a cell is not particularly limited, and a person skilled in the art will appropriately determine culture conditions (culture medium composition, temperature, pH and the like) that enable expression and/or secretion of the insulin resistance marker (the aforementioned polynucleotide and/or the aforementioned polypeptide).

More concretely, a function of an insulin resistance marker refers to an insulin resistance-inducing activity. As the insulin resistance-inducing activity, for example, an activity of suppressing the insulin signaling pathway and the glucose transport system may be recited. Such an activity refers to, for example, an activity that suppresses an increase of phosphorylated Akt mediated by an insulin receptor, or increases or decreases the other factor that functions downstream Akt in the insulin signal pathway and a glucose transport carrier so that glucose transport from outside the cell is suppressed. These functions are acquired owing to constant presence of the insulin resistance marker.

In this method, a substance that suppresses the aforementioned function by an insulin resistance marker is selected.

The "Akt" is a serine/threonine kinase also called PKB or protein kinase B.

The "phosphorylated Akt" is activated form of the Akt.

The "factor that functions downstream Akt in the insulin signaling pathway" means a factor involved in a series of route (namely, a glucose transport system) from activation by phosphorylated Akt to uptake of glucose into the cell in the insulin signaling pathway. As the glucose transport carrier, a glucose transport protein such as GLUT-4 is recited.

In this case, selection of a substance that controls a function of the insulin resistance marker of the present invention may be achieved in the following manner.

For example, a substance may be selected based on an increase in a level of phosphorylated Akt in the insulin resistance sample that is brought into contact with the candidate substance, compared with a level of phosphorylated Akt in the insulin resistance sample that is not brought into contact with the candidate substance; or a reduction in an expression level of phosphorylated Akt expressed in an insulin resistance cell that is brought into contact with the candidate substance, compared with a level of phosphorylated Akt in an insulin resistance cell that is not brought into contact with the candidate substance, as one index.

For example, when using a cell that requires an expression inducing substance (for example, TNFα, a glucocorticoid (dexamethasone), a free fatty acid, resistin, PAI-1 and so on) for expression of an insulin resistance marker, a substance may be selected based on a reduction in an expression level of phosphorylated Akt expressed in an insulin resistance cell that is brought into contact with the candidate substance in the presence of the expression inducing substance, compared with a level of phosphorylated Akt in an insulin resistance cell that is not brought into contact with the candidate substance in the presence of the expression inducing substance, as an index.

Among the insulin signaling-related factors, as for the factor that activates the glucose transport system by its upregulation like the aforementioned phosphorylated Akt, a substance that controls a function of the insulin resistance marker may be selected in a similar manner as described above.

On the other hand, among the insulin signaling-related factors, as for the factor that inactivates the glucose transport system by its upregulation like Akt, a substance may be selected based on a reduction in the level of the factor in an insulin resistance sample that is brought into contact with the candidate substance, compared with the level of the factor in an insulin resistance sample that is not brought into contact with the candidate substance; or an increase in an expression level of the factor expressed in an insulin resistance cell that is brought into contact with the candidate substance, compared with a level of the factor in an insulin resistance cell that is not brought into contact with the candidate substance, as one index.

4. Pharmaceutical Composition for Improving Insulin Resistance

The pharmaceutical composition in the present invention may be used as a diagnostic drug for evaluating insulin resistance, and as a potential or practical therapeutic drug for improving the insulin resistance.

The insulin resistance marker of the present invention, and a substance selected by the above screening method are useful as active ingredients of the pharmaceutical composition.

In other words, as an active ingredient of the pharmaceutical composition of the present invention, the following are recited. The pharmaceutical composition may be prepared by mixing a pharmaceutically acceptable diluent, carrier, excipient and so on, into such an active ingredient.

4-1. Polypeptide Comprising at Least any 15 Continuous Amino Acids in the Amino Acid Sequence Represented by SEQ ID NO: 1

A possible form of a polypeptide capable of binding with a ligand competitively with a polypeptide comprising at least any 15 continuous amino acids in the amino acid sequence represented by SEQ ID NO: 1, which is an insulin resistance marker of the present invention, enables therapy when it is administered. Therefore, a pharmaceutical composition containing the polypeptide as an active ingredient is useful as a therapeutic agent.

4-2. Antibody Against Polypeptide Comprising at Least any 15 Continuous Amino Acids in the Amino Acid Sequence Represented by SEQ ID NO: 1

The "antibody" includes a polyclonal antibody, a monoclonal antibody and an antibody prepared by a molecular biological technique. Preparation of these antibodies is conducted by a method well known to a person skilled in the art.

The "Antibody" broadly refers to a substance that binds immune specifically, and includes antibody fragments and antibody-fused proteins.

As is described in the aforementioned method of evaluating insulin resistance, an antibody against a polypeptide comprising at least any 15 continuous amine acids in the amino acid sequence represented by SEQ ID NO: 1, which is an insulin resistance marker of the present invention, is usefully used for evaluation of insulin resistance. Therefore, a pharmaceutical composition containing the polypeptide as an active ingredient is useful as a therapeutic drug.

Since the antibody specifically binds with the polypeptide comprising at least any 15 continuous amino acids in the amino acid sequence represented by SEQ ID NO: 1, which is an insulin resistance marker of the present invention, it is possible to attenuate the function of the insulin resistance marker. Therefore, the pharmaceutical composition containing the peptide as an active ingredient is useful as a therapeutic drug.

4-3. Substance That Controls Expression Level or Secretion Level of Polypeptide Comprising at Least any 15 Continuous Amino Acids in the Amino Acid Sequence Represented by SEQ ID NO: 1

This substance is selected by the method of screening a substance that improves insulin resistance as described above, and as described as to the method, the substance reduces an expression amount or a secretion amount of a polypeptide comprising at least any 15 continuous amino acids in the amino acid sequence represented by SEQ ID NO: 1, which is an insulin resistance marker of the present invention. Therefore, a pharmaceutical composition containing the substance as an active ingredient is useful as a therapeutic drug.

4-4. Substance That Controls Function by Polypeptide Comprising at Least any 15 Continuous Amino Acids in the Amino Acid Sequence Represented by SEQ ID NO: 1

This substance is selected by the method of screening a substance that improves insulin resistance as described above, and as is already described as to the method, the substance attenuates the function of the polypeptide comprising at least any 15 continuous amino acids in the amino acid sequence represented by SEQ ID NO: 1, which is an insulin resistance marker of the present invention. Therefore, a pharmaceutical composition containing this substance as an active ingredient is useful as a therapeutic drug.

As such a substance, the one that increases a substance that controls an insulin signaling-related factor which is downregulated by expression or secretion of a polypeptide which is an insulin resistance marker of the present invention, or the one that reduces a substance that controls an insulin signal-related factor which is upregulated by expression or secretion of a polypeptide which is an insulin resistance marker of the present invention may be recited, as described as to the method.

4-5. Polynucleotide Selected From the Group Consisting of Polynucleotide Comprising at Lease any 45 Continuous Bases in the Base Sequence Represented by SEQ ID NO: 2 and Polynucleotide Complementary to the Polynucleotide When the polynucleotide which is an insulin resistance marker of the present invention is employed as target RNA, double-stranded RNA having a sequence homology with the target RNA (this is also included in the polynucleotide provided as an insulin resistance marker of the present invention) is able to induce dissociation of the target RNA by an RNA interference mechanism. Therefore, the pharmaceutical composition containing the polynucleotide as an active ingredient is useful as a therapeutic agent.

Also, when this polynucleotide which is an insulin resistance marker of the present invention is employed as a target, a polynucleotide that is complementary to the target polynucleotide is able to inhibit activation of a gene when it is administered. Therefore, the pharmaceutical composition that contains the polynucleotide as an active ingredient is useful as a therapeutic agent.

4-6. Substance That Controls Expression Level of Polynucleotide Selected from the Group Consisting Of Polynucleotide Comprising at Least any 45 Continuous Bases in the Base Sequence Represented by SEQ ID NO: 2 and Polynucleotide Complementary to the Polynucleotide This substance is selected by a method of screening a substance that improves insulin resistance as described above, and as described as to the method, reduces an expression amount of a polynucleotide selected from the group consisting of a polynucleotide comprising at least any 45 continuous bases in the base sequence represented by SEQ ID NO: 2, which is an insulin resistance marker of the present invention, and a polynucleotide complementary to the polynucleotide. Therefore, a pharmaceutical composition containing the substance as an active ingredient is useful as a therapeutic agent.

EXAMPLES

In the following, the present invention will be described concretely by way of examples, which are not intended to limit the present invention.

Reference Example 1

Differentiation into Adipocyte

Mouse 3T3-L1 cells (ATCC No. CCL-92.1.) were added with Dulbecco's modified Eagle's medium-low glucose (Wako Pure Chemical Industries, Ltd.), 10% bovine serum (GIBCO BRL), and a penicillin/streptomycin solution (GIBCO BRL), and cultured at 37° C. in 5% carbon dioxide.

After reaching confluent, the cells were further cultured for two days. Then the medium was replaced by a differentiation inducing medium. As the differentiation inducing medium, Dulbecco's modified Eagle's medium-high glucose (Wako Pure Chemical Industries, Ltd.) added with 10% fetal bovine serum, a penicillin/streptomycin solution (GIBCO BRL), 0.5 mM 1-methyl-3-isobutylxanthine, 1 μM dexamethasone, and 5 μg/mL insulin was used.

After three days, the medium was replaced by Dulbecco's modified Eagle's medium-high glucose (Wako Pure Chemical Industries, Ltd.), 10% fetal bovine serum, a penicillin/streptomycin solution (GIBCO BRL), and 5 μg/mL insulin, and cultured for two days. Thereafter, the medium was replaced every two days. As the adipocyte maintenance medium, Dulbecco's modified Eagle's medium added with 10% fetal bovine serum, and a penicillin/streptomycin solution (GIBCO BRL) was used.

After the aforementioned differentiation inducing treatment, lipid droplets were formed in the cells on the fourth day, and 80% or more of the cells were confirmed to be differentiated into matured adipocytes containing lipid droplets on the eighth day.

Reference Example 2

Induction of Insulin Resistance

Using the matured adipocyte at the eighth or later day after the differentiation inducing treatment, the cells were cultured in an adipocyte maintenance medium added with 20 nM dexamethasone for eight days to induce insulin resistance, and an adipocyte in which insulin resistance was induced by dexamethasone was obtained. On the other hand, using the matured adipocyte at the eighth or later day after the differentiation inducing treatment, the cells were cultured for four days in an adipocyte maintenance medium added with 4 ng/mL TNFα to induce insulin resistance, and an adipocyte in which insulin resistance was induced by TNFα was obtained.

Example 1

Expression Variation Analysis of Proepithelin Protein by NBS Method (i) Isotope Labeling Method (NBS(2-nitrobenzenesulfenyl) Method The adipocyte in which insulin resistance was induced by the method described in Reference Example 2 was solubilized using 6 M guanidine hydrochloride, 50 mM Tris-hydrochloride (pH 8.0), 2 mM EDTA, 1 mM PMSF, 10 μg/mL leupeptin, and 10 μg/mL aprotinin, and a protein was extracted. Each 200 μg of the extracted protein was labeled at tryptophan residues with the use of an NBS labeling kit (SHIMADZU BIOTECH).

On the other hand, an adipocyte in which insulin resistance was not induced obtained by the method of Reference Example 1 was labeled with a 12C-NBS reagent (12C-NBS labeling), and prepared as a control group (Control).

The adipocyte in which insulin resistance was induced by TNFα, and the adipocyte in which insulin resistance was induced by dexamethasone were respectively labeled with a stable isotope (13C-NBS labeling) using a 13C-NBS reagent. Further, the respective 13C-NBS-labeled proteins were mixed with an equivalent amount of the control group, and fragmented by trypsin, to obtain digests including 13C-NBS-labeled peptide and 12C-NBS-labeled peptide (these are collectively called an "NBS-labeled peptide").

For the obtained digests, a treatment was conducted according to the protocol of the NBS labeling kit, and the NBS-labeled peptide was concentrated. Further, the NBS-labeled peptide was fractionated by using LC-10ADvp-μHPLC system (SHIMADZU CORPORATION), and each fraction was directly dispensed into a MALDI-TOF MS targeting plate using Accuspot LC spotting system (SHIMADZU CORPORATION). Comparative quantification analysis between 12C-NBS-labeled peptide and 13C-NBS-labeled peptide was conducted from the results obtained by automatic analysis of MALDI-TOF MS (AXIMA-CFR Plus; SHIMADZU CORPORATION) by using pair peak analyzing software (TWIP).

(ii) Identification of Proepithelin Protein by Mass Spectrometry

In the analytical result obtained in the above (i), for peaks in which the intensity of 13C-NBS-labeled peptide (derived from an insulin resistance adipocyte) relative to that of 12C-NBS-labeled peptide (derived from a normal adipocyte) showed a difference of 1.25 times or more, MS/MS analysis was conducted to identify the protein. Concretely, MS/MS analysis was conducted using AXIMA-QIT (SHIMADZU CORPORATION), and the obtained spectrum data was subjected to an MS/MS ion search using a mascot research engine (Matrix Science), and searched for public gene and protein sequence databases such as NCBI.

The above step was conducted for each of the adipocytes in which insulin resistance was induced by TNFα and the adipocyte in which insulin resistance was induced by dexamethasone in triplet independent experiments. As a result, a novel insulin resistance-related protein proepithelin exhibiting a significant ($p$ value<0.05) upregulation in both of adipocytes in which insulin resistance was induced was identified.

The result obtained in this example (result of expression variation analysis of a proepithelin protein by the NBS method) is shown in FIG. 1. In FIG. 1, the vertical axis represents the relative intensity (the intensity in an insulin resistance adipocyte relative to the intensity in a normal adipocyte), and for each of an adipocyte in which insulin resistance was induced by TNFα (TNFα), and an adipocyte in which insulin resistance was induced by dexamethasone (DEX), the relative intensities in proepithelin (aa297-309: an enzyme digestion fragment corresponding to a partial sequence of an epithelin-4 peptide constituting a proepithelin protein) and a house keeping protein GA DPH (aa308-321) for comparison are shown based on a quantified value of the NBS-labeled peptide (NBS Labeled Peptide) (mean value±standard deviation (mean±S.D.), n=4, p-value: **<0.05).

As shown in FIG. 1, the NBS method revealed that proepithelin (aa.297-309) increased significantly (p-value<0.05) in both of the insulin resistance adipocytes (TNFα: increased to 1.66 times, DEX: increased to 3.01 times).

Example 2

Analysis of Proepithelin Protein by Western Blotting Method

A matured adipocyte in which insulin resistance was induced by the method of Reference Example 2 was solubilized in a TNE buffer (1% (w/w) Nonidet P-40, 150 mM sodium chloride, 20 mM Tris-hydrochloride (pH 7.4), 2 mM EDTA, 10 μg/mL leupeptin, 10 μg/mL aprotinine, 5 mM mercaptoethanol, 1 mM PMSF, 1 mM Na3VO4, 10 μM sodium molybdate, and 50 mM sodium fluoride), and a protein was extracted. The extracted protein was separated by SDS-polyacrylamide gel electrophoresis (SDS-PAGE), and then transferred to a polyvinylidene fluoride (PVDF) membrane or a nitrocellulose membrane. A goat anti-proepithelin antibody (R&D Systems) was used as a primary antibody, a rabbit anti-goat IgG HRP-labeled antibody (ZYMED) was used as a secondary antibody, and ECL Blotting Detection Reagents (GE Healthcare) were used for detection of an HRP-labeled antibody.

Figure 2A:
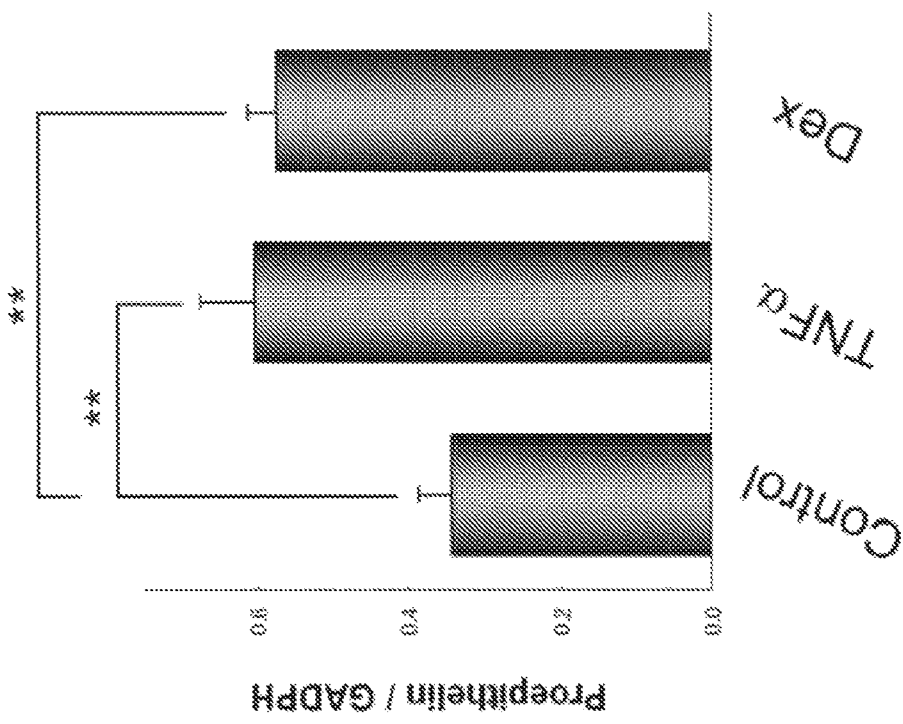
FIG. 2A and FIG. 2B show a result of analysis of expression variation of a proepithelin protein by the Western blotting method.
Figure 2B:
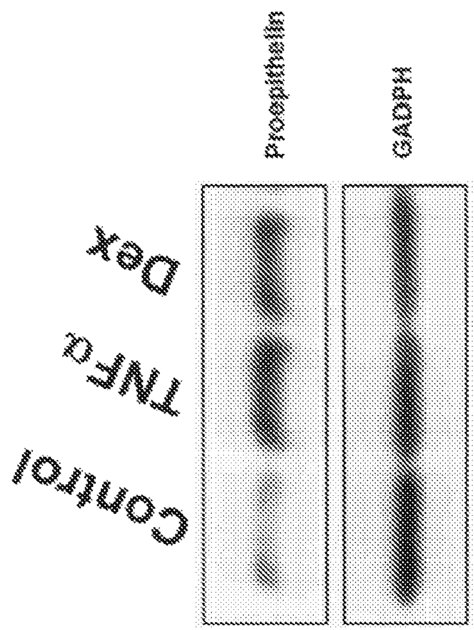

The result obtained in this example (analytical result of a proepithelin protein by the Western blotting method) is shown in FIG. 2. In FIG. 2A, the vertical axis represents a relative value of an expression amount of a proepithelin protein, relative to an expression amount of a house keeping protein GADPH, and for each of a control (Control), the adipocyte in which insulin resistance was induced by TNFα (TNFα), and the adipocyte in which insulin resistance was induced by dexamethasone (Dex), the relative value is shown (mean value±standard deviation (mean±S.D.), n=4, p-value: **<0.05). FIG. 2B shows Western blot images for proepithelin proteins obtained from respective extracts of insulin resistance adipocytes (TNFα and Dex) and the house keeping protein GADPH for comparison.

As shown in FIG. 2, also the Western blotting method using an antibody of a proepithelin protein, it was demonstrated that a proepithelin showed significant (p-value<0.05) upregulation in both of the insulin resistance adipocytes (TNFα: increased to 1.83 times, Dex: increased to 1.95 times).

Example 3

Figure 3:
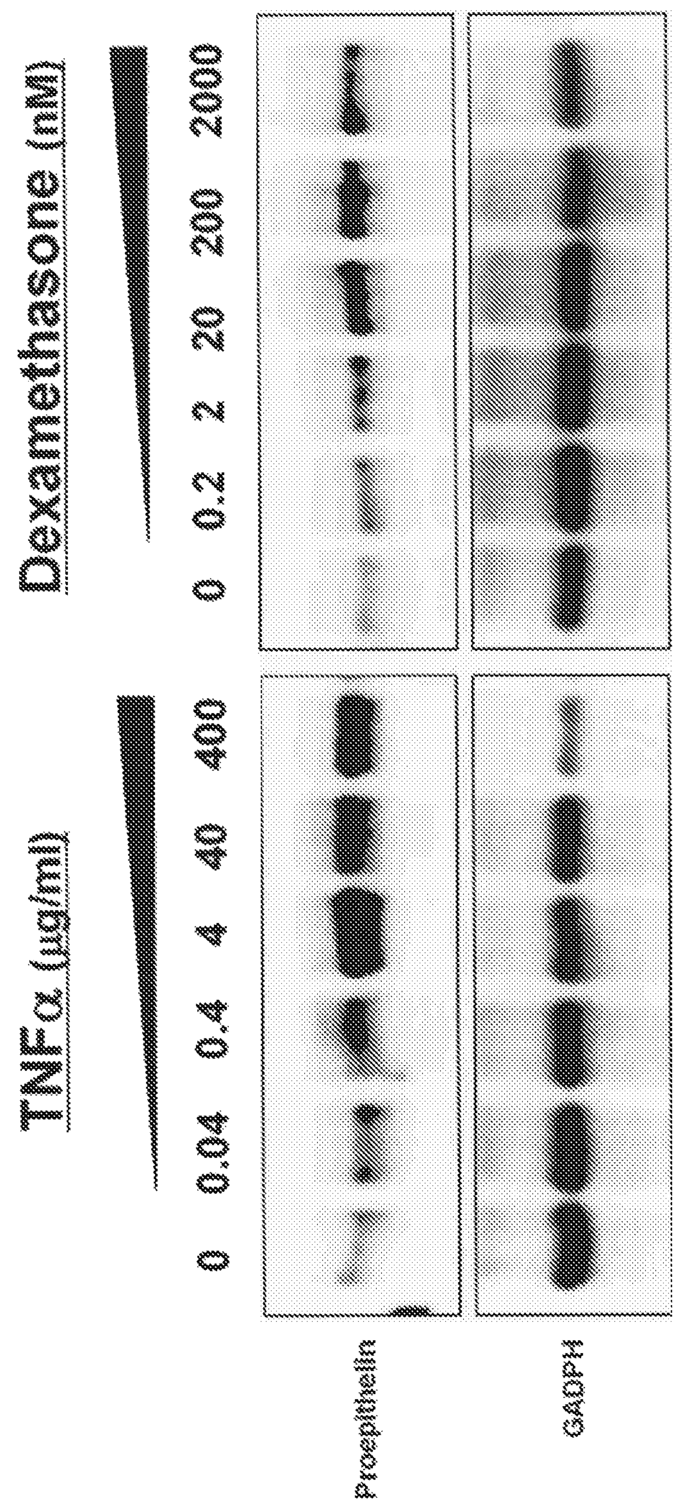
FIG. 3 shows variation in expression amount of a proepithelin protein with varied concentrations of TNFα and dexamethasone.

Variation in Expression of Proepithelin Protein with Concentrations of TNFα and Dexamethasone The same method as that in Reference Example 2 was conducted except that the concentration of TNFα (TNFα (ng/ml)) and the concentration of dexamethasone (Dexamethasone (nM)) used for induction of insulin resistance were changed, and various kinds of insulin resistance adipocytes were obtained. For such insulin resistance adipocytes, Western blotting was conducted in the same manner as that of Example 2 as described above. FIG. 3 shows Western blotting images for a proepithelin protein, and a house keeping protein GADPH for comparison. As shown in FIG. 3, it was demonstrated that an upregulation of a proepithelin protein was dependent on the concentration of TNFα and the concentration of dexamethasone.

Example 4

Variation in Expression of Proepithelin Protein in Adipose Differentiation

In the above Reference Example 1, cells were collected on the day when differentiation induction started (Day 0), on the fifth day when droplets started accumulating (Day 5), on the eighth day when the differentiation completed (Day 8), and on the tenth day (Day 10), on the twelfth day (Day 12), on the sixteenth day (Day 16), and on the twentieth day (Day 20).

Each cell is a cell in the course of differentiation of an undifferentiated preadipocyte having low insulin sensitivity (namely, insulin resistant) into a matured adipocyte. That is, the series of cells obtained in this manner are used as models of differentiation of an adipocyte.

Figure 4:
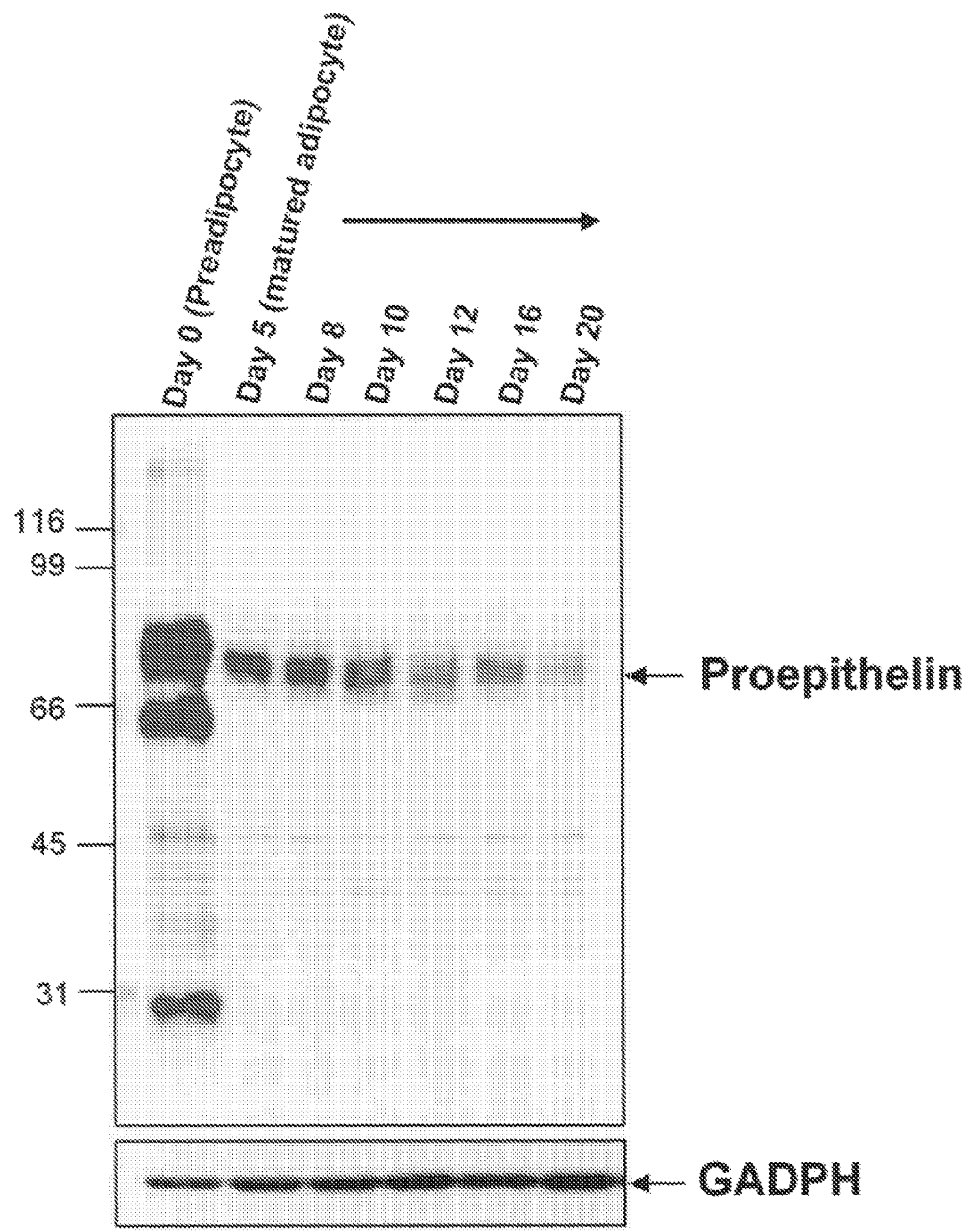
FIG. 4 shows variation in expression of a proepithelin protein in adipose differentiation.

Each cell was subjected to the Western blotting method in the same manner as in Example 1, and variation in an expression amount of a proepithelin protein was examined. The result is shown in FIG. 4 together with the result for the house keeping protein GADPH for comparison. As shown in FIG. 4, it was demonstrated that a proepithelin protein exhibited a very high expression level in a preadipocyte having low insulin sensitivity, and the expression significantly decreased as the adipose differentiation proceeded.

Therefore, from the foregoing Examples 2 and 3 (using an adipocyte in which insulin resistance is induced), and this Example 4 (using an adipocyte in which insulin resistance is not induced), it was demonstrated that an expression amount of a proepithelin protein has a direct relationship with insulin resistance (sensitivity) regardless of presence or absence of induction of insulin resistance.

Example 5

Effect of Thiazolidine Based Compound on Upregulation of Proepithelin Protein

In this example, an effect of pioglitazone on expression of proepithelin in induction of insulin resistance was examined using a thiazolidine based compound (pioglitazone), which is an insulin sensitizer.

For each of the adipocytes (TNFα, Dexamethasone) that were obtained by inducing insulin resistance by TNFα and dexamethasone according to the method of the foregoing Reference Example 2, and the adipocyte (Control) obtained by the method of Reference Example 1, the Western blotting method was conducted in the same manner as that of Example 2 for the cases where 10 μM pioglitazone was added (+pioglitazone (10 μM)) and not added (−pioglitazone (10 μM)). For the case where pioglitazone was added to an adipocyte having been subjected to a treatment of inducing insulin resistance, pioglitazone was added together with TNFα and dexamethasone.

Figure 5A:
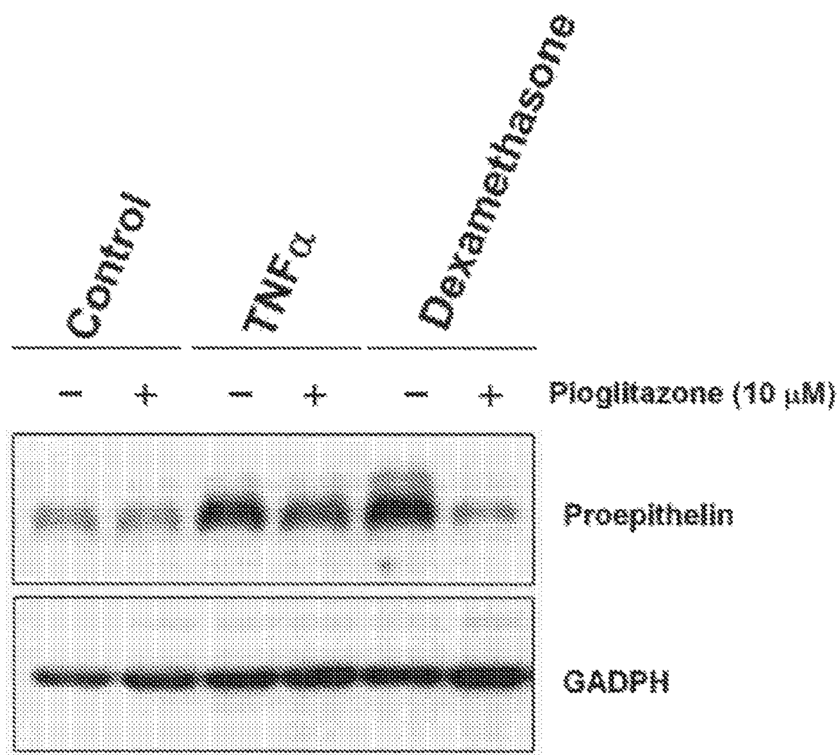
FIG. 5A and FIG. 5B show an effect of pioglitazone on an increase in expression of a proepithelin protein.
Figure 5B:
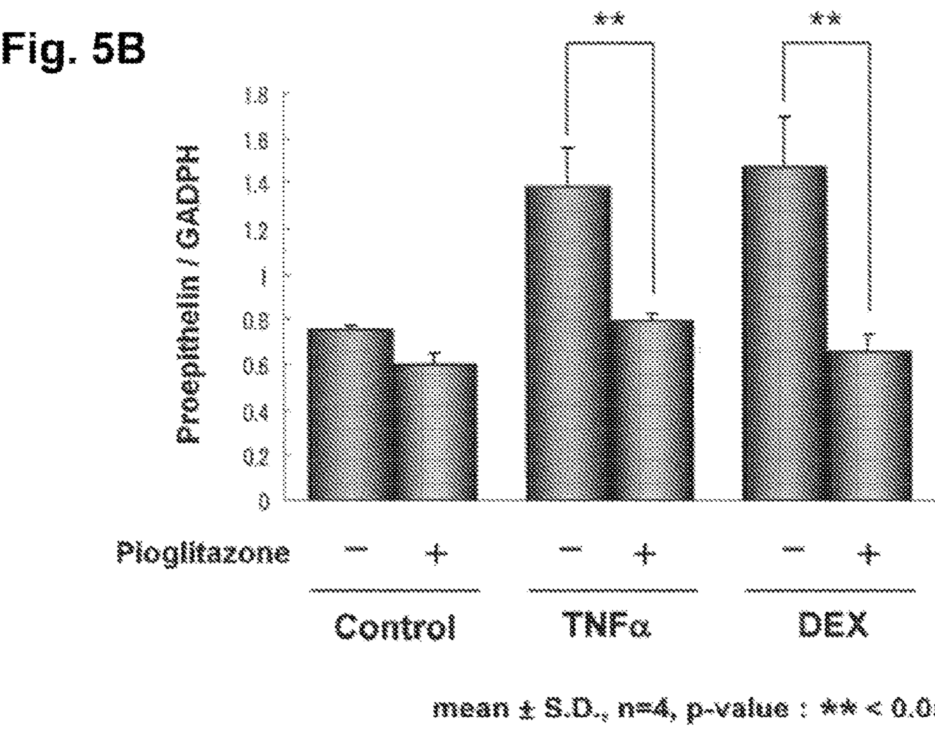

The obtained result (an effect of pioglitazone on an increase in expression of a proepithelin protein) is shown in FIG. 5. FIG. 5A shows western blotting images for a proepithelin protein and a house keeping protein GADPH for comparison. FIG. 5B is a graph showing a relative value of an expression amount of a proepithelin protein on the vertical axis, relative to an expression amount of GADPH (mean value±standard deviation (mean±S.D.), n=4, p-value: **<0.05). As shown in FIG. 5B, a proepithelin protein that exhibited a significant (p-value<0.05) upregulation by induction of insulin resistance was suppressed significantly (p-value<0.05), namely completely to the expression level equivalent to that of the control by a treatment with the insulin sensitizer. Therefore, these also demonstrated that an expression amount of a proepithelin protein has a direct relationship with insulin resistance.

Example 6

Effect of Proepithelin Protein on Insulin Signaling

A matured adipocyte prepared according to the method of Reference Example 1 was added with 100 nM insulin and a proepithelin protein (AdipoGen, Inc.) and cultured for 30 minutes, or added with 100 nM insulin without addition of proepithelin protein and cultured for 30 minutes to prepare an adipocyte (+100 nM Insulin) stimulated by insulin. When the proepithelin protein was added, concentrations of the proepithelin protein were 10 nM, 50 nM, 100 nM, and 200 nM.

The obtained adipocyte stimulated by insulin was solubilized in an RIPA buffer (1% (w/w) Triton X-100, 1% sodium deoxycholate, 0.1% sodium dodecylsulfate, 150 mM sodium chloride, 20 mM Tris-hydrochloride (pH 7.4), 2 mM EDTA, 10 μg/mL leupeptin, 10 μg/mL aprotinin, 5 mM mercaptoethanol, 1 mM PMSF, 1 mM Na3VO4, 10 μM sodium molybdate, 50 mM sodium fluoride), and proteins were extracted.

The extracted proteins were subjected to the Western blotting method. Concretely, following separation by SDS-polyacrylamide gel electrophoresis (SDS-PAGE), the protein was transferred to a polyvinylidene fluoride (PVDF) membrane or a nitrocellulose membrane. A rabbit anti-phosphorylated AKT (Ser473) antibody (Santa Cruz Technology) was used as a primary antibody, a goat anti-rabbit IgG HRP-labeled antibody (ZYMED) was used as a secondary antibody, and ECL Blotting Detection Reagents (GE Healthcare) were used for detection of an HRP-labeled antibody.

A matured adipocyte prepared according to the method of Reference Example 1 was added with a proepithelin protein (AdipoGen, Inc.) without addition of insulin, and cultured for 30 minutes, or cultured for 30 minutes without addition of both insulin and a proepithelin protein, to prepare an adipocyte not stimulated by insulin (−Insulin). When the proepithelin protein was added, concentrations of the proepithelin protein were 10 nM, 50 nM, 100 nM, and 200 nM.

For the obtained adipocyte not stimulated by insulin (−Insulin), protein extraction and Western blotting were conducted in the same manner as described above.

By examining an Akt phosphorylation level of an adipocyte stimulated by insulin (+100 nM Insulin) relative to an Akt phosphorylation level of an adipocyte not stimulated by insulin (−Insulin), activation of an insulin signal transduction system was examined. For detecting an Akt phosphorylation level, an Akt protein in which 473th serine is phosphorylated (pAkt-Ser473) was used as a detection target.

Figure 6:
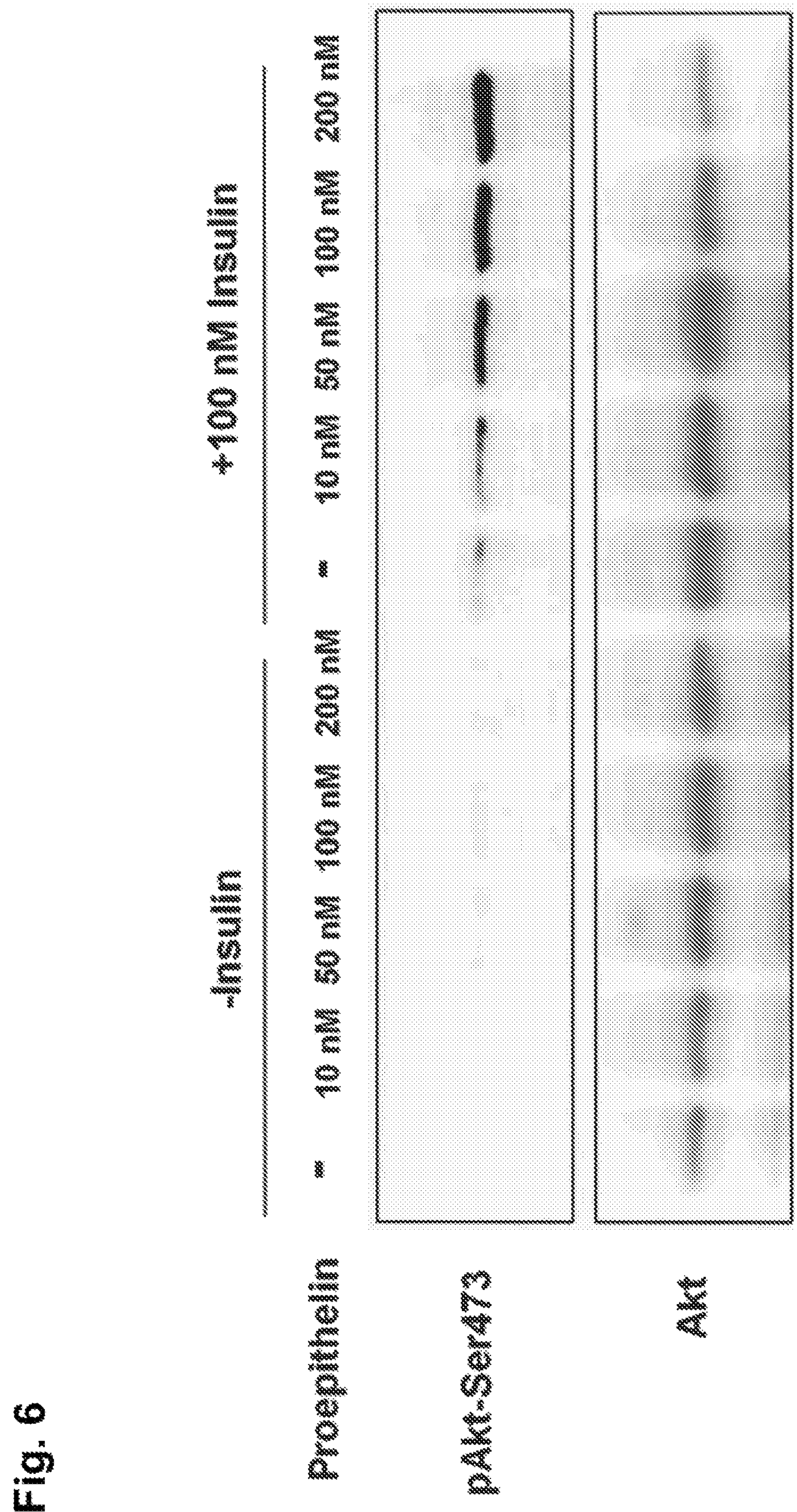
FIG. 6 shows an effect of insulin signal transduction by a proepithelin protein.

The obtained result is shown in FIG. 6. As shown in FIG. 6, a phosphorylation level at 473th serine in the Akt protein increased with the concentration of added proepithelin. The Akt protein is a protein kinase that acts downstream of the insulin receptor. Therefore, it was proved that a proepithelin protein has a function of facilitating insulin signaling.

Example 7

An Insulin Signaling-Suppressing Action by Constant Presence of Proepithelin Protein A matured adipocyte prepared according to the method of Reference Example 1 was added with a proepithelin protein (AdipoGen, Inc.) and incubated for 6 hours, and then added with 100 nM insulin and cultured for 30 minutes, or added with 100 nM insulin without addition of a proepithelin protein, and cultured for 30 minutes, to prepare an adipocytes stimulated by insulin (+100 nM Insulin). When the proepithelin protein was added, concentrations of the proepithelin protein were set at 50 nM, 100 nM, and 200 nM.

A matured adipocyte prepared according to the method of Reference Example 1 was added with a proepithelin protein (AdipoGen, Inc.) and cultured for 6 hours, or cultured for 30 minutes without addition of both insulin and a proepithelin protein, to prepare an adipocyte not stimulated with insulin (−Insulin). When the proepithelin protein was added, concentrations of the proepithelin protein were set at 50 nM, 100 nM, and 200 nM.

For each of the adipocyte stimulated by insulin (+100 nM Insulin) and the adipocyte not stimulated by insulin (−Insulin) obtained in the manner as described above, protein extraction and Western blotting were conducted in the same manner as in Example 6.

Figure 7:
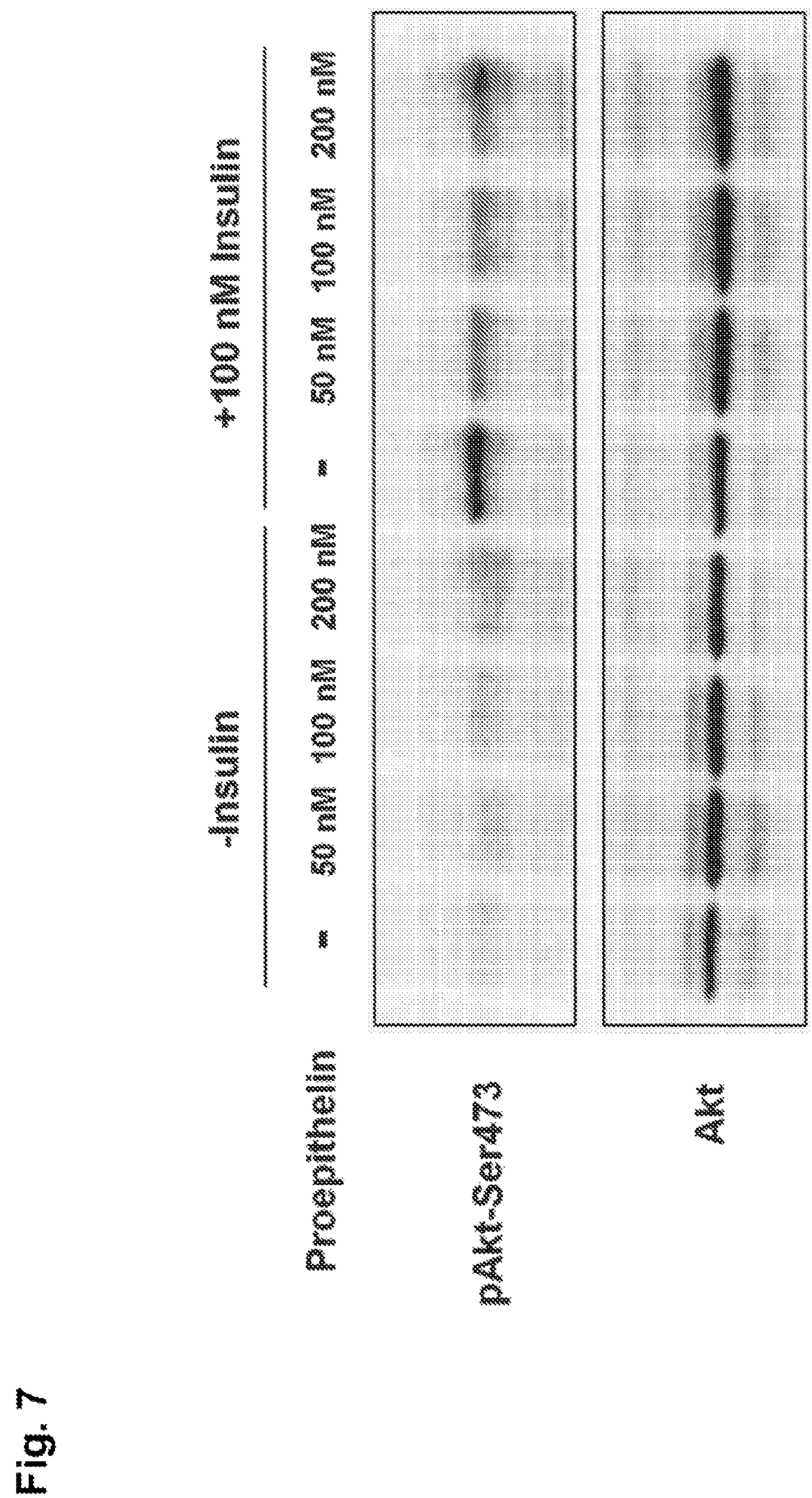
FIG. 7 shows an insulin signaling-suppressing action by constant presence of a proepithelin protein.

The obtained result is shown in FIG. 7. As shown in FIG. 7, by preliminarily treating an adipocyte using a proepithelin protein, a phosphorylation level of an Akt protein decreased. This reveals that insulin signaling is suppressed by constant presence of a proepithelin protein in the medium.

The result of Example 6 and the result of Example 7 showed that a proepithelin protein has an act of temporarily promoting insulin signaling, while it has an act of inhibiting insulin signaling when it is constantly present.

It is presumed that proepithelin has a function of promoting a proliferation signal such as insulin as one of its functions because proepithelin is a known protein having a proliferating activity likewise insulin, while it is also presumed that the function is reversed probably because of presence of an signaling pathway mediated by proepithelin and an insulin signal, and the path is somewhat controlled due to long-term exposure.

These results strongly suggest not only a relation between a proepithelin protein and insulin resistance but also a function of proepithelin protein direct on regulation of insulin sensitivity.

Figure 8:
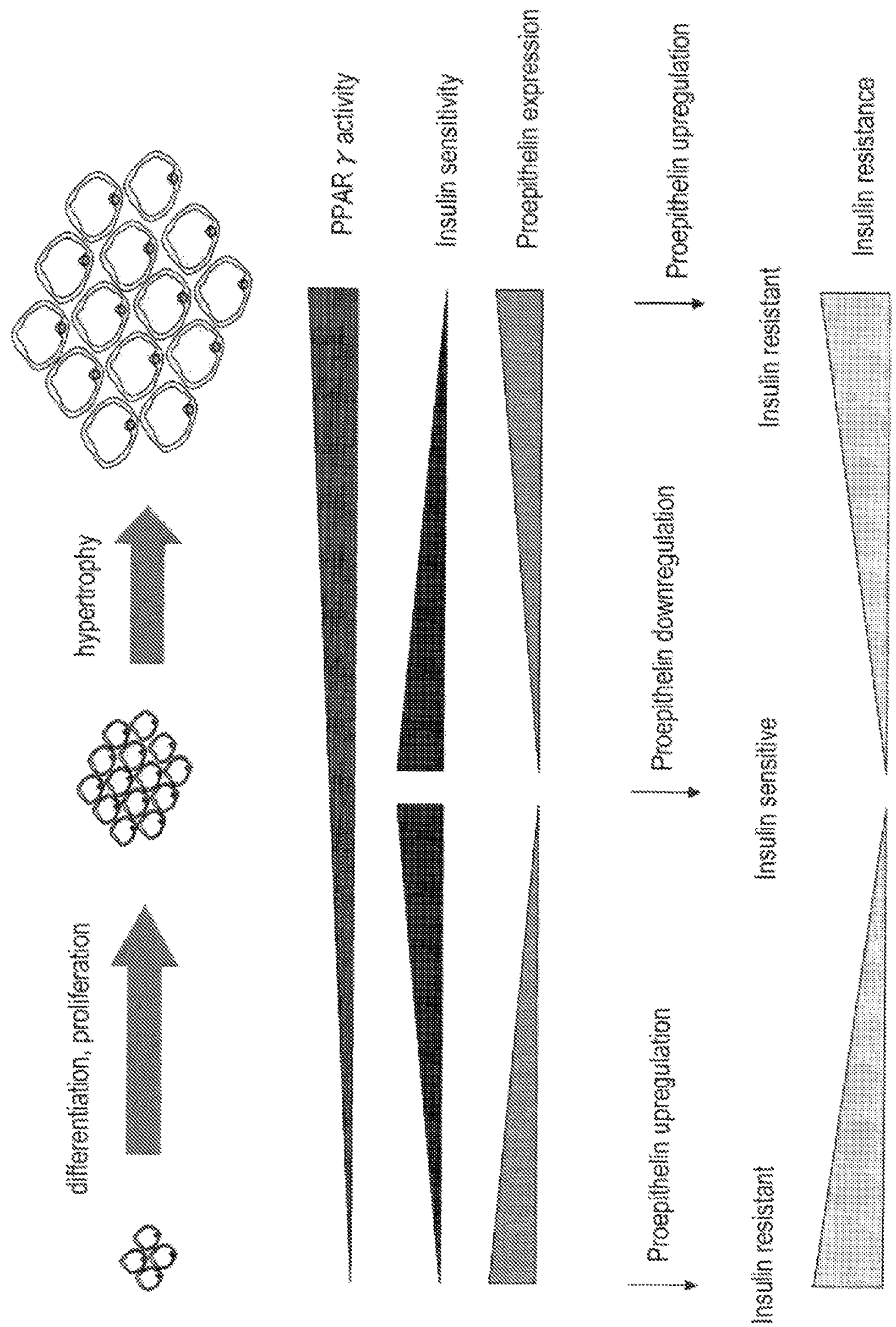
FIG. 8 is a schematic view about a relationship between a proepithelin protein and insulin resistance in an adipocyte.

A schematic view summarizing the series of results is shown in FIG. 8. As a conventional therapeutic method for insulin resistance, there has been considered a therapeutic method including promoting differentiation and miniaturization of an adipocyte by a thiazolidine derivative (PPARγ agonist) and releasing the insulin resistance again. On the other hand, as for proepithelin, the expression level and the secretion level decreased in the course of differentiation and proliferation of an adipocyte, so that it is expected that insulin sensitivity is imparted to an individual. In a hypertrophic adipocyte, TNFα is secreted excessively, and as a result, expression and secretion levels of proepithelin increase, and insulin resistance is initiated. In other words, there may be conceived a therapeutic method that cancels insulin resistance by suppressing expression and secretion levels of proepithelin or reducing the function.

The Examples described above show concrete embodiments within the scope of the present invention, but the present invention is not limited to these Examples and may be implemented in various embodiments. Therefore, the Examples described above are merely illustrative in every respect, and should not be construed as being restrictive. Further, the changes that fall within the equivalents of the claims are all within the scope of the present invention.

What is claimed is:

1. A method of screening a substance for improving cellular insulin resistance, comprising the steps of:

bringing an adipocyte capable of expressing or secreting a polypeptide having the amino acid sequence of SEQ ID NO: 1 into contact with a candidate substance to stimulate the adipocyte to express or secrete the polypeptide;

isolating the polypeptide by solubilizing the adipocyte and extracting the polypeptide;

fragmenting the resulting polypeptide having the amino acid sequence of SEQ ID NO: 1 using trypsin;

measuring a level of a polypeptide fragment consisting of 13 continuous amino acids 297-309 of SEQ ID NO: 1 in the adipocyte when the candidate substance is brought into contact; and comparing the measured level of the polypeptide fragment consisting of the 13 continuous amino acids 297-309 of SEQ ID NO: 1 in the adipocyte when the candidate substance is brought into contact, with an expression level or a secretion level of the polypeptide in the adipocyte when the candidate substance is not brought into contact, wherein a reduction of the measured level of the polypeptide fragment consisting of the 13 continuous amino acids 297-309 of SEQ ID NO:1 when the candidate substance is brought into contact, compared with the expression level or the secretion level when the candidate substance is not brought into contact, is regarded as one index for selecting the candidate substance as a substance that improves cellular insulin resistance, and wherein the step of bringing the adipocyte capable of expressing or secreting the polypeptide having the amino acid sequence of SEQ ID NO: 1 into contact with a candidate substance is conducted in vitro.

* * * * *